(12) United States Patent
Kauffmann

(10) Patent No.: US 11,971,415 B2
(45) Date of Patent: Apr. 30, 2024

(54) MICROALBUMIN CREATININE ASSAY DETECTION FLAG AND METHODS OF PRODUCTION AND USE RELATED THERETO

(71) Applicant: Siemens Healthcare Diagnostics Inc., Tarrytown, NY (US)

(72) Inventor: Aaron Kauffmann, Elkhart, IN (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 568 days.

(21) Appl. No.: 17/259,361

(22) PCT Filed: Jun. 20, 2019

(86) PCT No.: PCT/US2019/038181
§ 371 (c)(1),
(2) Date: Jan. 11, 2021

(87) PCT Pub. No.: WO2020/013970
PCT Pub. Date: Jan. 16, 2020

(65) Prior Publication Data
US 2021/0302430 A1    Sep. 30, 2021

Related U.S. Application Data

(60) Provisional application No. 62/697,672, filed on Jul. 13, 2018.

(51) Int. Cl.
*G01N 33/58* (2006.01)
*B01L 3/00* (2006.01)
*G01N 33/70* (2006.01)

(52) U.S. Cl.
CPC .............. *G01N 33/58* (2013.01); *B01L 3/502* (2013.01); *G01N 33/70* (2013.01); *B01L 2300/16* (2013.01); *B01L 2400/0406* (2013.01)

(58) Field of Classification Search
None
See application file for complete search history.

(56) References Cited

U.S. PATENT DOCUMENTS 4,189,536 A * 2/1980 Green ...................... C12Q 1/50
                                                                    435/14
5,385,847 A * 1/1995 Yip ..................... G01N 33/6827
                                                                    435/7.1

(Continued)

FOREIGN PATENT DOCUMENTS

EP        0330517 A2    8/1989
JP     2003520942 A    7/2003

(Continued)

OTHER PUBLICATIONS

T.G. Chasteen, "Capillary Electrophoresis", 2005, Sam Houston State University (Year: 2005).*

(Continued)

*Primary Examiner* — Maris R Kessel
*Assistant Examiner* — Mickey Huang

(57) ABSTRACT

Devices, kits, and methods related to embodiments of an improved liquid test sample injection device comprising a sample mixture that comprises at least one sample flag compound for detecting the presence or non-presence of a patient's liquid test sample upon being interrogated by a pre-determined wavelength of light.

12 Claims, 17 Drawing Sheets

(56) References Cited

U.S. PATENT DOCUMENTS

| | | | |
|---|---|---|---|
| 5,464,777 A * | 11/1995 | Yip | G01N 33/70 |
| | | | 435/7.1 |
| 5,624,850 A | 4/1997 | Kumar et al. | |
| 5,976,896 A | 11/1999 | Kumar et al. | |
| 6,670,115 B1 * | 12/2003 | Zhang | G01N 33/5438 |
| | | | 436/538 |
| 2007/0131565 A1 | 6/2007 | Fujiwara et al. | |
| 2009/0157025 A1 | 6/2009 | Song et al. | |
| 2010/0108513 A1 | 5/2010 | Amirkhanian | |
| 2016/0011178 A1 | 1/2016 | Hoenes et al. | |

FOREIGN PATENT DOCUMENTS

| | | |
|---|---|---|
| JP | 2011007717 A | 1/2011 |
| JP | 2017514107 A | 6/2017 |
| WO | 2005054840 A1 | 6/2005 |
| WO | 2016012778 A1 | 1/2016 |

OTHER PUBLICATIONS

International Search Report and Written Opinion of International Application No. PCT/US2019/038181 dated Oct. 22, 2019.
European Search Report and Written Opinion of European Application No. 19833097.9 dated Jul. 27, 2021.

* cited by examiner

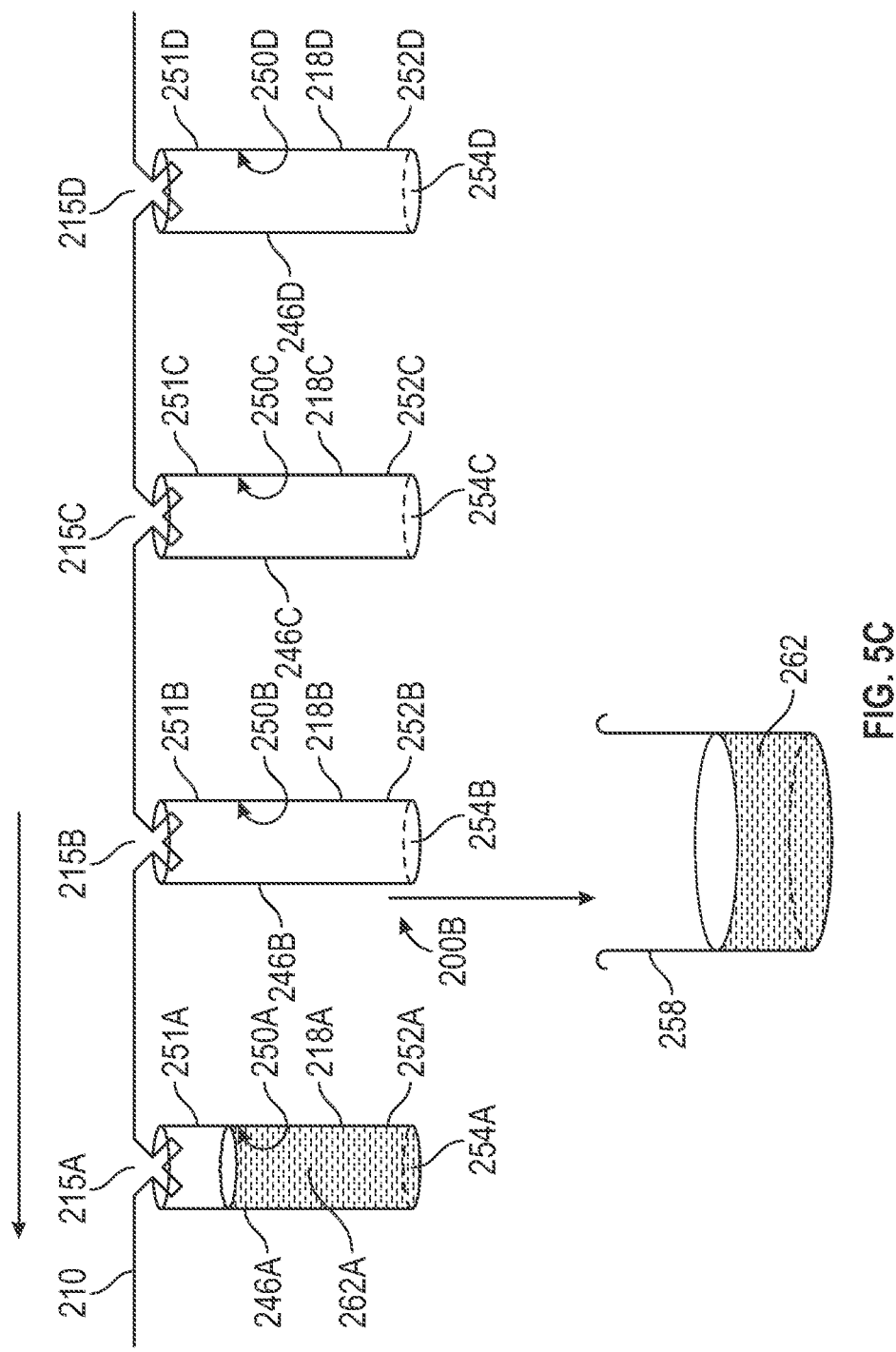

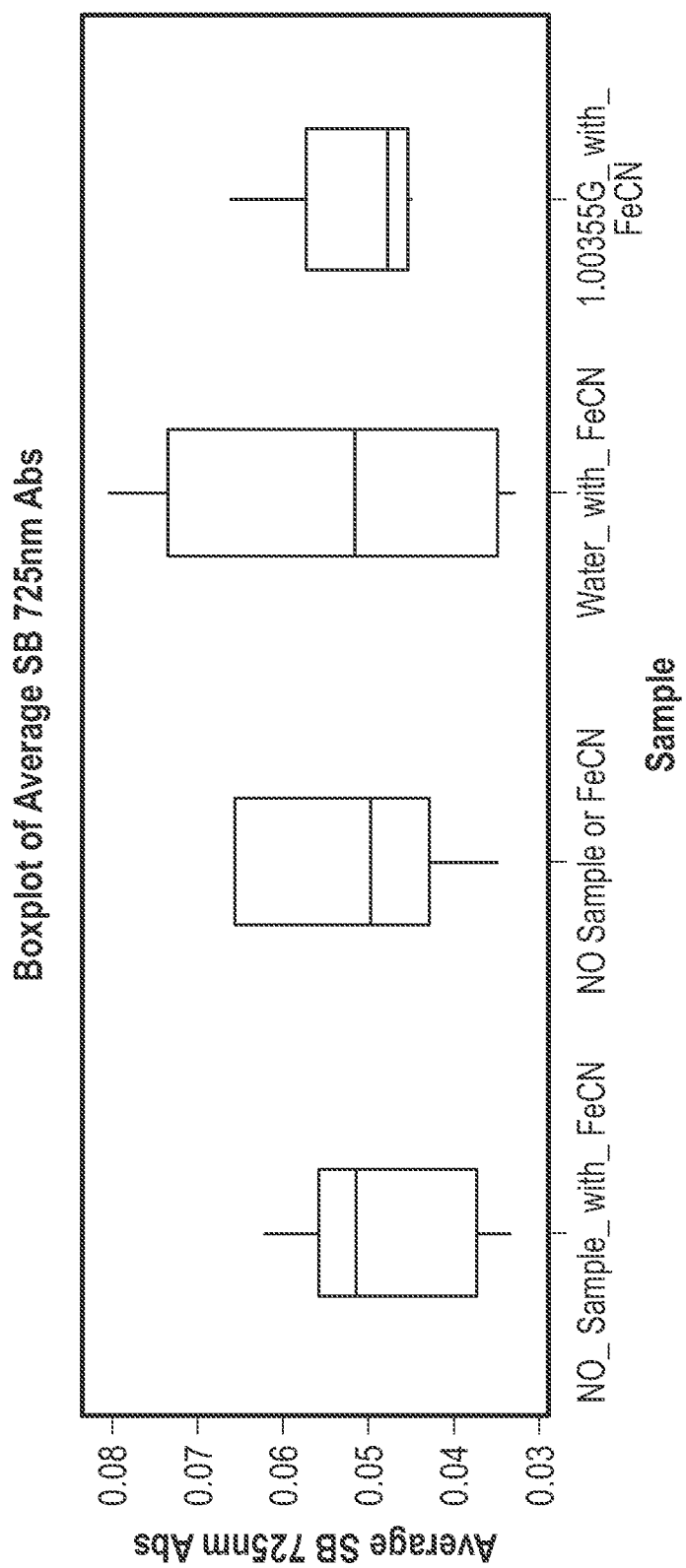

MICROALBUMIN CREATININE ASSAY DETECTION FLAG AND METHODS OF PRODUCTION AND USE RELATED THERETO

CROSS REFERENCE TO RELATED APPLICATIONS

The subject application claims benefit under 35 USC § 119(e) of U.S. provisional Application No. 62/697,672, filed Jul. 13, 2018. The entire contents of the above-referenced patent application are hereby expressly incorporated herein by reference.

STATEMENT REGARDING FEDERALLY FUNDED RESEARCH OR DEVELOPMENT

Not Applicable.

TECHNICAL FIELD

The presently disclosed and claimed inventive concept(s) relate to a device(s), kit(s), and method(s) for detecting the presence or non-presence of a patient's liquid test sample utilized for the conductance of at least one diagnostic assay. More specifically, the presently disclosed and claimed inventive concept(s) relate to an improved device(s) comprising at least one sample flag compound for detecting the presence or non-presence of a patient's liquid test sample upon being interrogated by a pre-determined wavelength of light, as well as kits and methods of use related thereto.

BACKGROUND

Numerous devices, kits, and methods exist for conducting assays that detect analytes that may be present in a patient's liquid test samples. Such devices have been proven to be effective in diagnostic assays that detect the presence and quantity of certain analytes indicative of a patient's health, including, but not limited to, glycated hemoglobin (HbA1c), microalbumin and creatinine, and lipid-based analytes, such as cholesterol, triglycerides, and/or high-density lipoproteins. It is common that such devices utilize a capillary or capillary-like component for the injection of the patient's liquid test sample (for instance, by way of example only, a patient's urine sample) into a reaction cassette for the conductance of at least one automated diagnostic assay within an analyzer. However, these devices, kits, and methods are limited in that it is difficult for them to differentiate between the presence of a patient's dilute liquid test sample (dilute urine) and a capillary in which the operator neglected to add the patient's liquid test sample. Current methods and devices exist to detect the presence of a patient's liquid test sample in a diagnostic assay system, including cameras, submersible test strips, and/or reagent(s) stored in a sample read window(s). However, such current methods and devices are relatively expensive and require continual maintenance. Accordingly, a need exists for cost effective devices and methods that determine the presence or non-presence of a patient's liquid test sample prior to the initiation of at least one diagnostic test, such as, by way of example, a microalbumin creatinine test on a patient's urine sample. It is to such devices, kits, and methods that the presently disclosed and claimed inventive concept(s) is directed.

DESCRIPTION OF THE SEVERAL VIEWS OF THE DRAWINGS

FIGS. 5A-5H are perspective views of a non-limiting alternative embodiment of a method for coating at least one inner surface of a plurality of capillaries with a sample flag comprising a sample flag compound via fluid communication between the at least one inner surface of the plurality of capillaries with a solution in accordance with the presently disclosed and/or claimed inventive concept(s).

FIG. 11 depicts a boxplot graphical representation showing the average absorbance readings of various mixtures of a ferricyanide sample flag compound (with and without mixture of a patient's liquid test sample) at a wavelength of about 725 nanometers in accordance with the presently disclosed and/or claimed inventive concept(s).

DETAILED DESCRIPTION

Figure 1:
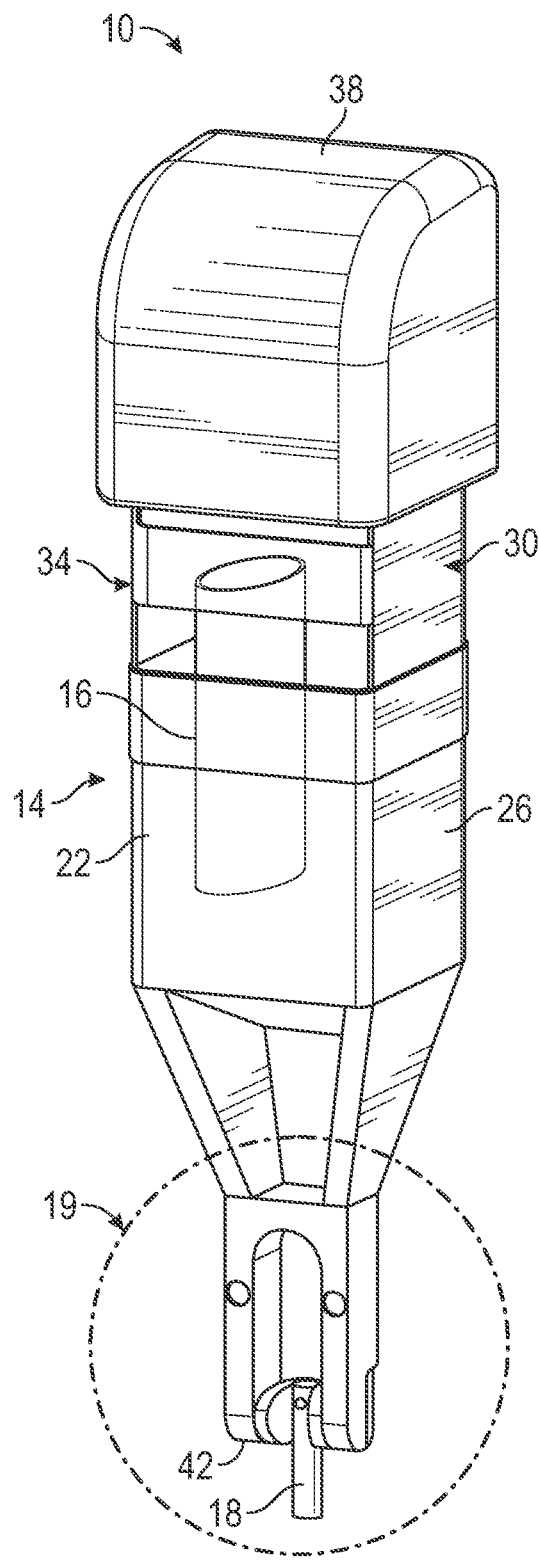
FIG. 1 is a perspective view of one non-limiting embodiment of a liquid test sample dispensing device utilized in accordance with the presently disclosed and/or claimed inventive concept(s).

Before explaining at least one embodiment of the inventive concept(s) in detail by way of exemplary drawings, experimentation, results, and laboratory procedures, it is to be understood that the inventive concept(s) is not limited in its application to the details of construction and the arrangement of the components set forth in the following description or illustrated in the drawings, experimentation and/or results. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well-known and commonly used in the art.

All patents, published patent applications, and non-patent publications mentioned in the specification are indicative of the level of skill of those skilled in the art to which this presently disclosed and claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the devices, kits, and/or methods disclosed and claimed herein can be made and executed without undue experimentation in light of the present disclosure. While the compositions and methods of this presently disclosed and claimed inventive concept(s) have been described in terms of preferred embodiments, it will be apparent to those of skill in the art that variations may be applied to the compositions and/or methods and in the steps or in the sequence of steps of the method described herein without departing from the concept, spirit and scope of the presently disclosed and claimed inventive concept(s). All such similar substitutes and modifications apparent to those skilled in the art are deemed to be within the spirit, scope and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The singular forms "a," "an," and "the" include plural referents unless the context clearly indicates otherwise. Thus, for example, reference to "a compound" may refer to 1 or more, 2 or more, 3 or more, 4 or more or greater numbers of compounds. The term "plurality" refers to "two or more." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. For example, but not by way of limitation, when the term "about" is utilized, the designated value may vary by ±20% or ±10%, or ±5%, or ±1%, or ±0.1% from the specified value, as such variations are appropriate to perform the disclosed methods and as understood by persons having ordinary skill in the art. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z. The use of ordinal number terminology (i.e., "first", "second", "third", "fourth", etc.) is solely for the purpose of differentiating between two or more items and is not meant to imply any sequence or order or importance to one item over another or any order of addition, for example.

As used in this specification and claim(s), the terms "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein, the phrase "associated with" includes both direct association of two moieties to one another as well as indirect association of two moieties to one another. Non-limiting examples of associations include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety.

The term "liquid test sample" as used herein will be understood to include any type of biological fluid sample that may be utilized in accordance with the presently disclosed and claimed inventive concept(s). Examples of biological samples that may be utilized include, but are not limited to, whole blood or any portion thereof (i.e., plasma or serum), saliva, sputum, cerebrospinal fluid (CSF), intestinal fluid, intraperotineal fluid, cystic fluid, sweat, interstitial fluid, tears, mucus, urine, bladder wash, semen, combinations, and the like. The volume of the sample utilized in accordance with the presently disclosed and claimed inventive concept(s) is from about 0.1 to about 100 microliters. As used herein, the term "volume" as it relates to the liquid test sample utilized in accordance with the presently disclosed and claimed inventive concept(s) means from about 0.1 microliter to about 100 microliters, or from about 1 microliter to about 75 microliters, or from about 2 microliters to about 60 microliters, or less than or equal to about 50 microliters, or less than or equal to about 40 microliters. In one non-limiting embodiment of the presently disclosed and/or claimed inventive concept(s), the liquid test sample is about 40 microliters of urine.

The term "sugar(s)" as used herein means any substance in the class of soluble, crystalline carbohydrates that comprise monosaccharides, disaccharides, oligosaccharides, polysaccharides, and combinations thereof. Non-limiting examples of sugars utilized in accordance with the presently disclosed and/or claimed inventive concept(s) include, but are not limited to, fructose, galactose, glucose, lactose, maltose, sucrose, and combinations thereof. In one non-limiting embodiment, the sugar comprises and/or consists of sucrose.

The terms "alcohol(s)" and/or "alcohol solvent(s)" as used herein means any organic compound in which at least one hydroxyl functional group (—OH) is bound to at least one carbon atom. Non-limiting examples of alcohols which may be utilized in accordance with the presently disclosed and/or claimed inventive concept(s) include, but are not limited to, monohydric, polyhydric, unsaturated aliphatic, alicyclic alcohols, and combinations thereof, including, without limitation, methanol, ethanol, propanol, butanol, pentanol, cetyl alcohol, ethylene glycol, propylene glycol, glycerol, erythritol, xylitol, mannitol, volemitol, allyl alcohol, geraniol, propargyl alcohol, inositol, menthol, and combinations thereof.

The term "sample flag compound(s)" as used herein means a compound(s) that emits a detectable signal, such as, by way of example, an absorbance change, when interrogated by a specific wavelength of visible light (for instance, by way of example only, a 425-nanometer wavelength of light) in the presence of a patient's liquid test sample. Non-limiting examples of sample flag compound(s) utilized in accordance with the presently disclosed and/or claimed inventive concept(s) include, but are not limited to, ferricyanide (FeCN)-containing compounds (such as, by way of example only, potassium ferricyanide), metabisulfite, taurine, and other sulfur-based and/or sulfur-containing compound(s).

The terms "capillary action" and/or "capillary force" as used herein will be understood to include the interaction between contacting surfaces of a liquid and a solid that distorts the liquid surface from a planar shape and causes the liquid to rise, fall, or remain contained in a narrow tube, channel, and/or cavity. By way of example only, and not by way of limitation, capillary action includes: (1) the wicking of a solution comprising a sample flag compound, at least one protein (such as, by way of example only, bovine serum albumin (BSA)), at least one sugar, and at least one alcohol into the capillary of the liquid test sample dispensing device; and (2) the wicking of the patient's liquid test sample into the capillary of the liquid test sample dispensing device, such that the liquid test sample remains in the capillary until agitated.

The term "patient" includes human and veterinary subjects. In certain embodiments, a patient is a mammal. In certain other embodiments, the patient is a human. "Mammal" for purposes of treatment refers to any animal classified as a mammal, including human, domestic and farm animals, nonhuman primates, and zoo, sports, or pet animals, such as dogs, horses, cats, cows, etc.

The term "reaction vessel" includes any device(s) capable of performing at least one diagnostic assay as described herein. The reaction vessel may perform the diagnostic assay(s) manually, but, in most instances, the reaction vessel will be inserted into a system that automates the performance of the diagnostic assay(s). In one non-limiting embodiment, the reaction vessel comprises a reaction cassette for use in automated diagnostic assays conducted by the DCA Vantage® Analyzer commercially available from Siemens Healthcare Diagnostics, Inc.; however, a person having ordinary skill in the art should readily appreciate that the presently disclosed and/or claimed inventive concept(s) can be utilized on any diagnostic assay system that conducts at least one diagnostic assay on a patient's liquid test sample.

Turning now to particular embodiments, the presently disclosed and claimed inventive concept(s) relate to a device(s), kit(s), and method(s) for chemically-detecting the presence or non-presence of a patient's liquid test sample which may be contained in a specimen holder, such as, by way of example only, a capillary. More specifically, the presently disclosed and claimed inventive concept(s) relate to an improved device(s) comprising at least one chemical flag for detecting the presence or non-presence of a patient's liquid test sample within a specimen holder upon the specimen holder being interrogated by a pre-determined wavelength of light, as well as kits and methods of use related thereto.

It is contemplated that virtually any reagent used in the fields of biological, chemical, or biochemical analyses and assays could be used in the devices, kits, and methods of the presently claimed and disclosed inventive concept(s). It is contemplated that these reagents may undergo physical and/or chemical changes when bound to an analyte of interest whereby the intensity, nature, frequency, or type of signal generated by the reagent-analyte complex is directly proportional or inversely proportional to the concentration of the analyte existing within the fluid sample. These reagents may contain indicator dyes, metal, enzymes, polymers, antibodies, and electrochemically reactive ingredients and/or chemicals that, when reacting with an analyte(s) of interest, may exhibit change in color.

Any method of detecting and measuring the analyte in a fluid sample can be used in the devices, kits, and methods of the presently claimed and inventive concepts. A variety of assays for detecting analytes are well known in the art and include, but are not limited to, chemical assays, enzyme inhibition assays, antibody stains, latex agglutination, latex agglutination inhibition and immunoassays, such as, radioimmunoassays. The term "antibody" herein is used in the broadest sense and refers to, for example, intact monoclonal antibodies, polyclonal antibodies, multi-specific antibodies (e.g., bispecific antibodies), and to antibody fragments that exhibit the desired biological activity (e.g., antigen/analyte-binding). The antibody can be of any type or class (e.g., IgG, IgE, IgM, IgD, and IgA) or sub-class (e.g., IgG2, IgG3, IgG4, IgA1, and IgA2).

While immunoassays (including, but not limited to, sequential analytical chemical and immunoassays) are primarily discussed herein for the detection of at least one analyte of interest present in a liquid test sample, a person having ordinary skill in the art should readily understand that the presently disclosed and claimed inventive concept(s) are not strictly limited to immunoassays and may include, by way of example and not by limitation, chemical and chemical-based assays, nucleic acid assays, lipid-based assays, and serology-based assays. Immunoassays, including radioimmunoassays and enzyme-linked immunoassays, are useful methods for use with the presently claimed and disclosed inventive concepts. A variety of immunoassay formats, including, for example, competitive and non-competitive immunoassay formats, antigen/analyte capture assays and two-antibody sandwich assays can be used in the methods of the invention. Enzyme-linked immunosorbent assays (ELISAs) can be used in the presently claimed and disclosed inventive concepts, as well. In the case of an enzyme immunoassay, an enzyme is typically conjugated to a second antibody, generally by means of glutaraldehyde, periodate, hetero-bifunctional crosslinking agents, or biotin-streptavidin complexes. As will be readily recognized, however, a wide variety of different conjugation techniques exist which are readily available for use with the presently disclosed and claimed inventive concept(s) to one skilled in the art.

Assays, including, but not limited to, immunoassays, nucleic acid capture assays, lipid-based assays, and serology-based assays, can be developed for a multiplexed panel of proteins, peptides, and nucleic acids which may be contained within a liquid test sample, with such proteins and peptides including, for example but not by way of limitation, albumin, microalbumin, cholesterol, triglycerides, high-density lipoproteins, low-density lipoproteins, hemoglobin, myoglobin, α-1-microglobin, immunoglobins, enzymes, proteins, glycoproteins, protease inhibitors, drugs, cytokines, creatinine, and glucose. The device(s), kit(s), and method(s) disclosed and/or claimed herein may be used for the analysis of any liquid test sample, including, without limitation, whole blood, plasma, serum, or urine. In one non-limiting embodiment, the liquid test sample is about 40 microliters of urine.

Referring now to the Figures, and more particularly to FIG. 1, shown therein is a non-limiting embodiment of a liquid test sample dispensing device 10 that both collects a patient's liquid test sample and dispenses the patient's liquid test sample into a reaction vessel for the conductance of at least one diagnostic assay. The liquid test sample dispensing device 10 comprises a body 14, a liquid waste collector 16, and a capillary 18.

In one non-limiting embodiment, and as shown in FIG. 1, the body 14 comprises a first side 22, a second side 26, a third side 30, a fourth side 34, a first end 38, and a second end 42. While depicted in FIG. 1 as comprising four sides, it should be readily understood that the body 14 can comprise any number of sides that accomplishes the presently disclosed and/or claimed inventive concept(s), including, without limitation, the body 14 may comprise 1, 2, 3, 4, 5, 6, 7, 8, 9, 10, 11, 12, 13, 14, 15, 16, 17, 18, 19, 20, 30, 40, 50, 60, 70, 80, 90, or greater than or equal to 100 sides. In addition, while shown in FIG. 1 as being substantially rectangular in shape, the body 14 can be configured to be any shape that accomplishes the presently disclosed and/or claimed inventive concept(s), including, without limitation, cylindrical, ovular, triangular prism, cube, rectangular prism, trapezoidal prism, pentagonal prism, hexagonal prism, heptagonal prism, octagonal prism, nonagonal prism, decagonal prism, or any polygonal prism (in which case, the number of sides will comport with the particular shape of the body 14—i.e., an octagonal prism-shaped body 14 comprises eight sides/faces). As shown in greater detail in FIG. 4, the body 14 of the liquid test sample dispensing device 10 is configured so as to be received in a reaction vessel wherein a patient's liquid test sample is dispensed from the capillary 18 into the reaction vessel for the conductance of at least one diagnostic assay, such as, by way of example only, a microalbumin creatinine diagnostic assay.

In certain non-limiting embodiments, the body 14 (and/or the capillary 18) is fabricated as a molded, unitary component formed of a rigid plastic material (so as to avoid deformation of the body 14 when both collecting a patient's liquid test sample and/or inserting the body into a reaction vessel), including, for example, synthetic and/or naturally-occurring or derived polymers (both organic and/or inorganic), such as, by way of example only, thermoplastic polymer(s), thermoset polymer(s), elastomer(s), and/or synthetic fiber(s) such as low-density polyethylene, high-density polyethylene, polystyrene, polyvinylchloride, styrene butadiene, acrylic(s), polyacrylics, and polyvinyl acetate, and/or soda-lime, and combinations thereof. However, a person having ordinary skill in the art should readily appreciate that the body 14 may be constructed of any material capable of accomplishing the presently disclosed and/or claimed inventive concept(s). In one non-limiting embodiment (as shown in FIG. 1), the body 14 of the liquid test sample dispensing device 10 is constructed such that the area defined by the first side 22, second side 26, third side 30, and fourth side 34 of the body 14 is hollow, in which the liquid waste collector 16 resides. In one non-limiting embodiment, the first side 22 and the third side 30 are open such that the liquid waste produced as a by-product during the conductance of at least one diagnostic assay is brought into contact with the liquid waste collector 16 for the removal and containment of the liquid waste; however, a person having ordinary skill in the art should readily understand that any or all of the sides of the body 14 may be open to allow for the interface between the liquid waste and the liquid waste collector 16.

In another non-limiting embodiment, the area defined by the first side 22, second side 26, third side 30, and fourth side 34 of the body 14 need not be hollow (or include the liquid waste collector 16). For instance, by way of example only, the area defined by the first side 22, second side 26, third side 30, and fourth side 34 of the body 14 may be solid, with no hollow spaces defined therein. In addition, rather than comprising the liquid waste collector 16, a plurality of microcavities (not shown) may be disposed on and formed in one or all of the first side 22, second side 26, third side 30, and fourth side 34 of the body 14 for the collection of liquid waste produced as a by-product of conducting at least one diagnostic assay.

The liquid waste collector 16 is adapted to and formed of a material(s) that collects the liquid waste produced as a by-product of conducting at least one diagnostic assay. While shown in FIG. 1 as being substantially cylindrical in shape, a person having ordinary skill in the art should understand that the liquid waste collector 16 can be any shape capable of accomplishing the presently disclosed and/or claimed inventive concept(s), including, without limitation, triangular prism, cube, rectangular prism, trapezoidal prism, pentagonal prism, hexagonal prism, heptagonal prism, octagonal prism, nonagonal prism, decagonal prism, or any polygonal prism (in which case, the number of sides will comport with the particular shape of the liquid waste collector 16—i.e., an octagonal prism-shaped liquid waste collector 16 comprises eight sides/faces). The liquid waste collector 16 can be constructed of any material or combination of materials that accomplishes the presently disclosed and/or claimed inventive concept(s), namely the absorbance and containment of liquid waste (which comprises a combination of used and unused diagnostic assay reaction reagents and the patient's liquid test sample). Such materials include, but are not limited to, cellulosic or fiber-based products, including, without limitation, paper, cotton, sponge, and cellulose acetate, as well as polymeric materials, including superabsorbent polymers, and any combinations of any of the above.

The capillary 18 is adapted to collect a patient's liquid test sample and to subsequently dispense/inject the liquid test sample into a reaction vessel. In addition, as shown in greater detail in FIG. 3A, the capillary 18 is adapted to collect a solution comprising and/or consisting of, in one non-limiting embodiment, a sample flag compound, at least one protein (such as, by way of example only, bovine serum albumin (BSA)), at least one sugar, and at least one alcohol. In one non-limiting embodiment, the capillary 18 collects the solution and the patient's liquid fluid sample via capillary action when the capillary 18 is in contact with the solution and/or the patient's liquid test sample, respectively. However, a person having ordinary skill in the art should readily appreciate that the solution and/or the patient's liquid test sample can be collected by the capillary 18 via any method commonly known in the art, including, without limitation, via creation of a negative pressure differential that draws either the solution and/or the patient's liquid test sample into the capillary 18. The capillary 18 can be constructed of any material(s) commonly known in the art, including, without limitation, glass and/or chemically-inert plastic(s). The size and volume-capacity of the capillary 18 will vary depending on: (1) the volume of solution necessary to substantially uniformly coat at least one inner surface of the capillary 18; and (2) the type and quantity of the patient's liquid test sample being collected. In certain non-limiting embodiments, the capillary 18 may be adapted and sized to hold volumes of from about 0.1 microliter to about 100 microliters, or from about 0.5 microliters to about 95 microliters, or from about 1 microliter to about 90 microliters, or from about 2 microliters to about 85 microliters, or from about 5 microliters to about 80 microliters, or from about 10 microliters to about 75 microliters, or from about 15 microliters to about 70 microliters, or from about 20 microliters to about 65 microliters, or from about 25 microliters to about 60 microliters, or from about 30 microliters to about 55 microliters, or from about 35 to about 50 microliters, or less than or equal to about 40 microliters. By way of example only, and not by way of limitation, the volume capacity of the capillary 18 is about 40 microliters when the patient's liquid test sample is urine. In one non-limiting embodiment, and as shown in greater detail in FIGS. 2 and 3A-3D, a first end 51 of the capillary 18 extends through the second end 42 of the body 14 wherein at least a portion of the capillary 18 remains external to the body 14 for collection of the solution and/or the patient's liquid test sample.

In addition, while depicted in FIG. 1 as being substantially cylindrical in shape, it should be readily understood to a person having ordinary skill in the art that the capillary 18 may be any shape capable of accomplishing the presently disclosed and/or claimed inventive concept(s), including, without limitation, triangular prism, cube, rectangular prism, trapezoidal prism, pentagonal prism, hexagonal prism, heptagonal prism, octagonal prism, nonagonal prism, decagonal prism, or any polygonal prism (in which case, the number of sides will comport with the particular shape of the capillary 18—i.e., an octagonal prism-shaped capillary 18 comprises eight sides/faces). In one non-limiting embodiment, the capillary 18 is substantially cylindrical in shape. In addition, the capillary 18 is adapted to receive liquid materials via capillary action.

Figure 2:
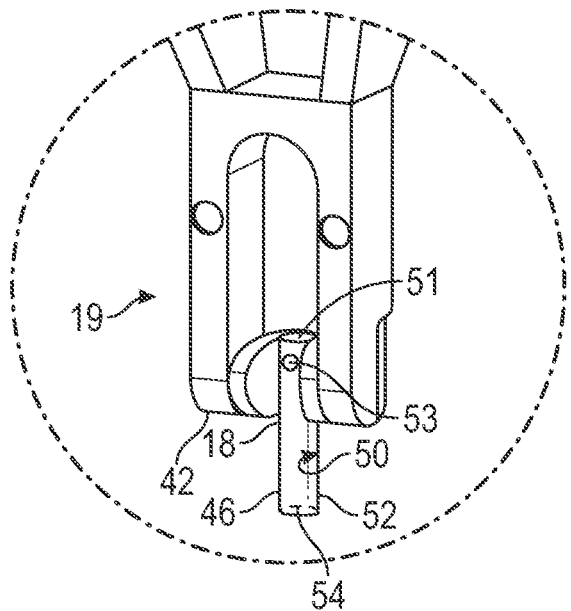
FIG. 2 is an enlarged, perspective view of the capillary portion of the liquid test sample dispensing device of FIG. 1.

Referring now to FIG. 2, shown therein is an enlarged, perspective view of the capillary portion 19 of the improved liquid test sample dispensing device 10 of FIG. 1. As shown in FIG. 2, the capillary portion 19 comprises the capillary 18, the capillary 18 further comprising at least one outer surface 46, at least one inner surface 50, a first end 51, a second end 52, a starch plug 53, and an opening 54 located at the second end 52 for receiving and dispensing a patient's liquid test sample and/or the solution via, by way of example only, capillary action.

Figure 3A:
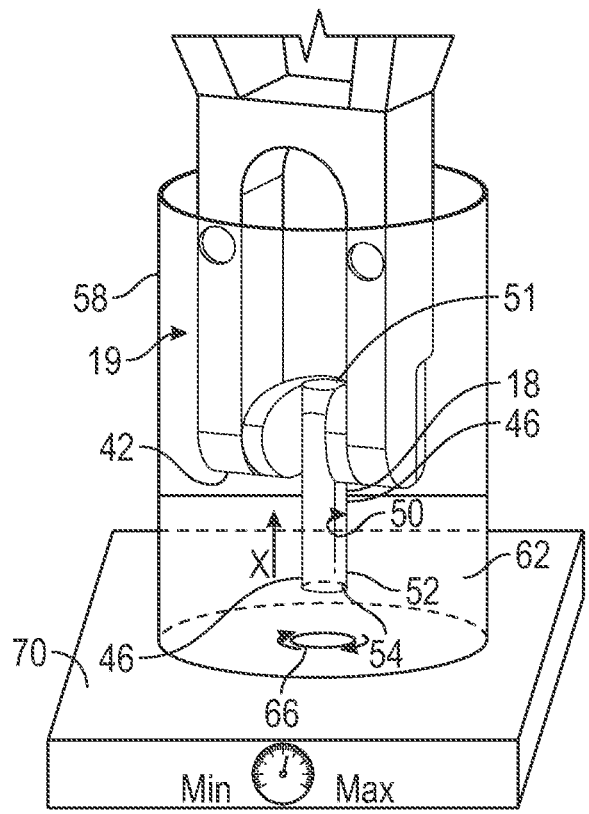
FIG. 3A is a perspective view of the capillary portion of FIG. 2 in which at least one inner surface of the capillary is in fluid contact with a solution in accordance with the presently disclosed and/or claimed inventive concept(s).

Referring now to FIG. 3A, shown therein is a perspective view of the capillary portion 19 of FIG. 2 in which the at least one inner surface 50 of the capillary 18 is in fluid contact with a solution 62 comprising and/or consisting of a sample flag compound, at least one protein (such as, by way of example only, bovine serum albumin (BSA)), at least one sugar, and at least one alcohol. As previously discussed with respect to FIG. 2, the capillary portion 19 comprises the capillary 18, the capillary 18 further comprising at least one outer surface 46, at least one inner surface 50, a first end 51, a second end 52, and an opening 54 at the second end 52.

In one non-limiting embodiment of the presently disclosed and/or claimed inventive concept(s), the solution 62 is formed from the combination two or more separate solutions. By way of example only, the solution 62 may be formed from the combination of a first solution comprising and/or consisting of a sample flag compound, at least one protein, and at least one sugar and a second solution comprising and/or consisting of at least one alcohol (or other water-soluble compound with low sample flag compound solubility). In one non-limiting embodiment, the first solution comprises potassium ferricyanide sample flag compound at a concentration of about 15 milligrams/milliliter, bovine serum albumin (BSA) at a concentration of about 6% based on the volume of the first solution, and sucrose at a concentration of about 15% based on the volume of the first solution. In one non-limiting embodiment, the second solution comprises methanol, ethanol, isopropyl alcohol, and/or combinations thereof. While certain non-limiting embodiments of the presently disclosed and/or claimed inventive concept(s) include specific amounts and/or concentrations of the constituents forming the first and second solutions (and the combined solution 62), a person having ordinary skill in the art should readily appreciate that the amounts and concentrations of the various constituents can be in any amount(s) and/or concentration(s) or ranges thereof capable of accomplishing the presently disclosed and/or claimed inventive concept(s). In one non-limiting embodiment, the ratio of the first solution to the second solution comprising the solution 62 is about 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20; however, a person having ordinary skill in the art should appreciate that the solution 62 may comprise any ratio of the first solution to the second solution provided that the solution 62 emits a detectable signal when interrogated with a certain wavelength of light (for instance, by way of example, a 425 nanometer wavelength of light) when the patient's liquid test sample is in fluid communication with the dried solution 62. In one non-limiting embodiment, the ratio of first solution to second solution in the solution 62 is about 1:12.57.

In one non-limiting embodiment, the volume of solution 62 present within the capillary 18 ranges from about 1 microliter to about 100 microliters, or from about 5 microliters to about 95 microliters, or from about 10 microliters to about 90 microliters, or from about 15 microliters to about 85 microliters, or from about 20 microliters to about 80 microliters, or from about 25 microliters to about 75 microliters, or from about 30 microliters to about 70 microliters, or from about 35 microliters to about 65 microliters, or from about 40 microliters to about 60 microliters, or from about 45 microliters to about 55 microliters, or greater than or equal to about 50 microliters. In one non-limiting embodiment of the presently disclosed and/or claimed inventive concept(s), the volume of solution 62 present within the capillary 18 is about 35 microliters.

In one non-limiting embodiment of the presently disclosed and/or claimed inventive concept(s), the capillary portion 19 is placed within a receptacle 58 containing the (as described elsewhere herein) combined solution 62 comprising and/or consisting of a sample flag compound, at least one protein, at least one sugar, and at least one alcohol. In order to ensure that the constituents remain equally dispersed throughout the solution 62, an inert stirring device, such as, by way of example only, an inert, magnetic stir bar 66 can be used in conjunction with a magnetic stirrer 70 for the continuous mixing of the solution 62 within the receptacle 58. Examples of commercially available magnetic stirrers are commonly known in the art. In addition, while shown in FIG. 3A as comprising a receptacle 58, a magnetic stir bar 66, and a magnetic stirrer 70, it should be readily understood to a person having ordinary skill in the art that the solution 62 may be mixed via any method commonly known in the art, including, by way of example only, via commercial-grade mixers that allow for the mixing of larger batches of the solution 62 in order to, as shown in greater detail in FIGS. 5A-5H, coat the internal surfaces of multiple capillaries simultaneously either via continuous or batch-processing methods. While shown in FIG. 3A as a single capillary 18, it should be readily understood to a person having ordinary skill in the art that the process of coating at least one inner surface 50 of the capillary 18 can be accomplished in a batch or continuous automated manufacturing process in which the inner surfaces of capillaries of multiple liquid test sample dispensing devices are simultaneously coated with the solution 62.

As shown in FIG. 3A, in one non-limiting embodiment, the capillary portion 19 is placed within the receptacle 58 such that the opening 54 of the capillary 18 is submerged within the solution 62. As a result of this submersion, the solution 62 wicks into the capillary 18 via capillary action (as shown by upward arrow x) through the opening 54 such that the solution 62 is in fluid communication with at least one portion of the inner surface 50 of the capillary 18. While shown in FIG. 3A as entering through the opening 54 via capillary action, a person having ordinary skill in the art should readily appreciate that the solution 62 need not be passively wicked into the capillary 18 through the opening 54; rather, the solution 62 may be actively injected into the capillary either through the opening 54 or during the manufacturing process of the capillary 18.

Figure 3B:
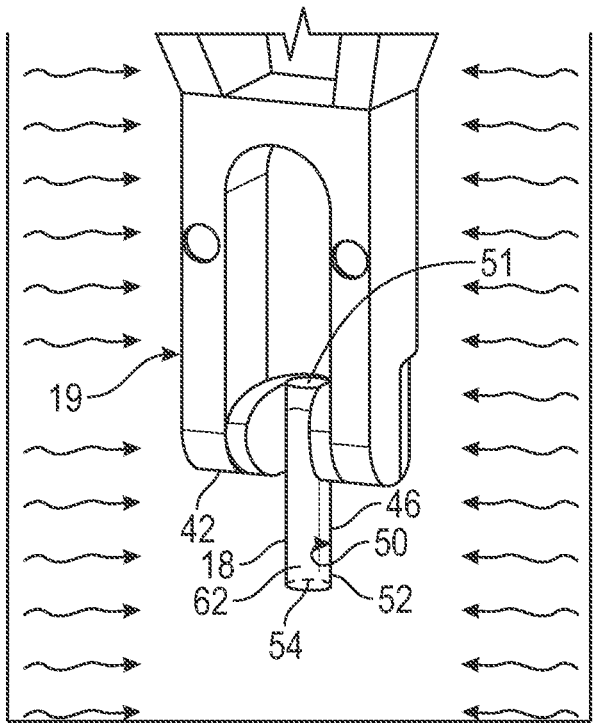
FIG. 3B is a perspective view of the capillary portion of FIG. 3A in which the liquid test sample dispensing device has been placed in a commercial-grade dryer to evaporate the at least one alcohol solvent from the solution in accordance with the presently disclosed and/or claimed inventive concept(s).

Referring now to FIG. 3B, once the solution 62 has been wicked into the capillary 18 via capillary action and is contained therein, the capillary portion 19 (or the entirety of the liquid test sample dispensing device 10) is, in one non-limiting embodiment, heated to evaporate off and remove the at least one alcohol solvent contained within the solution 62. The heating is conducted at a temperature that is high enough to evaporate the alcohol solvent, but low enough so as not to melt the sample flag compound which is deposited on the at least one inner surface 50 of the capillary 18 as the alcohol solvent evaporates. In one non-limiting embodiment, the at least one alcohol is selected from the group consisting of methanol, ethanol, isopropyl alcohol, and combinations thereof, and the solution 62 contained within the capillary 18 is heated to and maintained at a temperature from about 20° C. to about 100°, or from about 25° C. to about 95° C., or from about 30° C. to about 90° C., or from about 35° C. to about 85° C., or from about 40° C. to about 80° C., or from about 45° C. to about 75° C., or from about 50° C. to about 70° C., or from about 55° C. to about 65° C., or from about greater than or equal to 60° C. In one non-limiting embodiment, the capillary portion 19 is heated to a temperature in a range of from about 25° C. to about 37° C. to evaporate off and remove the alcohol solvent from the solution 62 contained within the capillary 18. The capillary portion 19 can be heated via any method commonly known in the art provided that the solution 62 remains in contact with the at least one inner surface 50 of the capillary 18 prior to and during the evaporation of the at least one insoluble volatile compound(s), including, without limitation, via commercial-grade dryers and/or vacuum dryers commonly known in the art. Additionally, the capillary portion 19 may not be heated at all, allowing for the evaporation of the at least one alcohol solvent to occur naturally under room temperature conditions.

In addition to alcohol solvent evaporation technique, the deposition of the sample flag compound(s) on at least one inner surface 50 of the capillary 18 may be accomplished via any methodology(-ies) that accomplish the presently disclosed and/or claimed inventive concept(s), including, without limitation: (1) inclusion of the sample flag compound(s) in the starch plug 53 (shown in greater detail in FIG. 2) during the manufacturing process of the liquid test sample dispensing device 10 (or the capillary 18, if manufactured separately)—the sample flag compound(s) diffusing out of the starch plug and mixing with the patient's liquid test sample when such liquid test sample is present within the capillary 18; and/or (2) the sample flag compound(s) may be incorporated into the material forming the capillary 18 during the manufacturing process of the liquid test sample dispensing device 10 (or the capillary 18, if manufacture separately).

Figure 4:
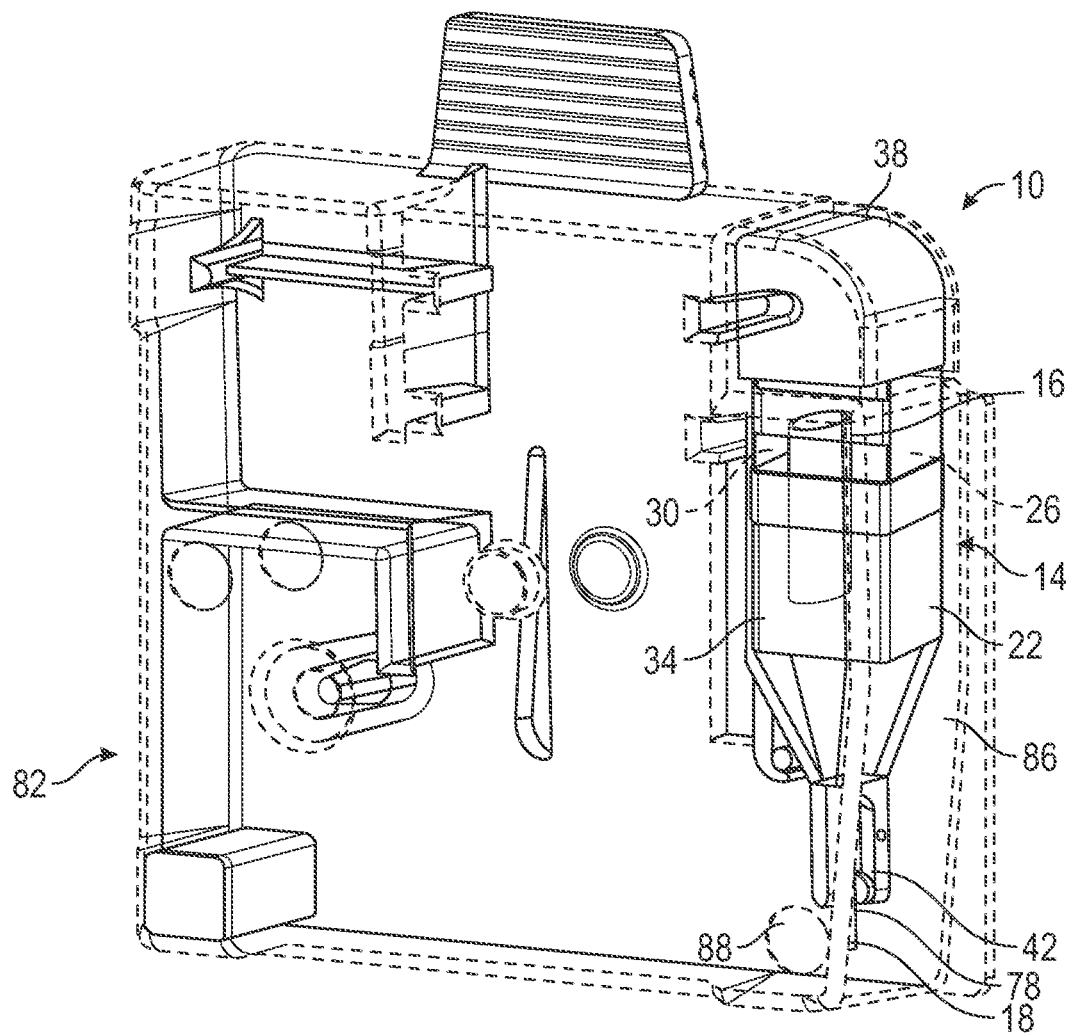
FIG. 4 is a perspective view of the liquid test sample dispensing device of FIG. 1 in which the at least one inner surface of the capillary is coated with a sample flag compound(s) in accordance with presently disclosed and/or claimed inventive concept(s) and the liquid test sample dispensing device has been inserted into a reaction vessel for the conductance of at least one diagnostic assay.

Referring now to FIG. 4, shown therein is a perspective view of the liquid test sample dispensing device 10 of FIG. 1 in which at least one inner surface 50 of the capillary 18 is coated with a sample flag compound(s) (as described elsewhere herein) and the liquid test sample dispensing device 10 has been inserted into a reaction vessel 82 for the conductance of at least one diagnostic assay. Following the collection of a patient's liquid test sample into the capillary 18 of the liquid test sample dispensing device 10, the patient's liquid test sample mixes with and dissolves the sample flag compound(s) deposited on the at least one inner surface 50 of the capillary 18 to form a sample mixture 78.

The liquid test sample dispensing device 10 is then inserted into and secured within a reaction chamber 86 of a reaction vessel 82.

Once secured within the diagnostic assay system/instrument, the capillary 18 is interrogated with a pre-determined wavelength of light via at least one system light source(s) (not shown) that passes through, by way of example only, a sample read window 88 of the reaction cassette 82 to interrogate the capillary 18. If the sample mixture 78 is present within the capillary 18 (even if the patient's liquid test sample within the sample mixture 78 is extremely dilute), a detectable signal is emitted from the sample mixture 78 (i.e., a change/shift in absorbance which can be measured by, for instance, a spectrophotometer which may be separate from or integrated into the diagnostic assay system/instrument) when interrogated with the particular wavelength of visible light from the light source(s). If the sample mixture 78 is not present within the capillary 18 (due to, by way of example only, the patient's liquid test sample either having not been collected in the capillary or if such liquid test sample has leaked out of the capillary 18 prior to insertion of the liquid test sample dispensing device 10 into the reaction chamber 86 of the reaction cassette 82), a detectable signal is not emitted when the capillary 18 is interrogated with the particular wavelength of visible light. Accordingly, the sample flag compound(s) are utilized as effective liquid test sample flags in which the presence of a patient's liquid test sample within a capillary 18 is verified prior to the conductance of at least one diagnostic assay within a diagnostic assay system/instrument (due to the emittance of a detectable signal when the sample mixture 78 is interrogated with a particular wavelength of visible light, such as, by way of example only, a 480 nanometer wavelength of light).

The diagnostic assay system/instrument may comprise any number of light sources that accomplishes the presently disclosed and/or claimed inventive concept(s), including, without limitation, 1, 2, 3, 4, 5, 6, 7, 8, 9, or equal to or greater than 10 light sources. In one non-limiting embodiment, the light source(s) is/are light emitting diode (LED) lights; however, a person having ordinary skill in the art should readily appreciate that the light source(s) need not be LED light(s) to accomplish the presently disclosed and/or claimed inventive concept(s) and can include, but not be limited to, incandescent bulb light sources, laser light sources, and any combinations thereof. In one non-limiting embodiment, the wavelengths of light generated by the various light source(s) are in the visible spectrum typically ranging from about 380 nanometers to about 800 nanometers. In one non-limiting embodiment, and as discussed in greater detail hereinbelow, the diagnostic assay system/instrument comprises and/or consists of at least three LED light sources emitting centroid wavelength values of about 425 nanometers, 536 nanometers, and 725 nanometers, respectively, in which the about 425 nanometer wavelength of light serves as a liquid test sample interrogator.

Once the presence of the patient's liquid test sample is verified via light interrogation, the sample mixture 78 (comprising the patient's liquid test sample) is then dispensed from the capillary 18 into the reaction chamber 86 of the reaction vessel 82 via, for example, the automated rotation and agitation of the reaction vessel 82 within the diagnostic assay system/instrument. Following the dispensing of the patient's liquid test sample into the reaction chamber 86 of the reaction vessel 82, at least one diagnostic assay (such as, by way of example only, microalbumin creatinine assay(s)) is conducted on the patient's liquid test sample. In one non-limiting embodiment, the at least one diagnostic assay involves pre-determined steps in which the reaction vessel 82 is rotated in both clockwise and counter clockwise directions such that the patient's liquid test sample is sufficiently mixed with both solid and liquid reagents associated with at least one diagnostic assay, while various measurements are taken at pre-determined intervals during the conductance of the at least one diagnostic assay. At the conclusion of the at least one diagnostic assay, a volume of liquid waste is contained within the reaction vessel 82, the volume of liquid waste primarily comprising a mixture of the patient's liquid test sample, the solid reagent(s), and/or the liquid reagent(s) utilized in the conductance of the at least one diagnostic assay. Subsequent to the conclusion of the at least one diagnostic assay, the reaction vessel 82 containing the volume of liquid waste is substantially inverted via, for example, rotation of the reaction vessel 82 within the diagnostic assay system/instrument. This inversion allows the volume of liquid waste to come into contact with the liquid waste collector 16, such that the volume of liquid waste is absorbed by and contained/maintained within the liquid waste collector 16.

While shown throughout the majority of the Figures as being connected to a liquid test sample dispensing device 10 when the solution 62 is, by way of example only, drawn, injected, and/or placed within the capillary 18 (thereby facilitating deposition of the sample flag (such as, by way of example only, a ferricyanide-containing compound) on at least one inner surface 50 of the capillary 18), it should be readily understood to a person having ordinary skill in the art that the capillaries may be separate from the liquid test sample dispensing device(s) when the solution is drawn into, injected into, and/or placed within the capillaries. In such instances, the capillaries can later be connected to the liquid test sample dispensing devices(s) or can be used for additional applications in accordance with the presently disclosed and/or claimed inventive concept(s).

FIGS. 5A-5H are perspective views of a non-limiting alternative embodiment of a method for coating at least one inner surface of a plurality of capillaries with a sample flag compound(s) via fluid communication between the at least one inner surface of the plurality of capillaries with a solution in accordance with the presently disclosed and/or claimed inventive concept(s). While FIGS. 5A-5H depict four separate capillaries, it should be readily understood to a person having ordinary skill in the art that the presently disclosed and/or claimed methodology can include any number of capillaries, for instance, by way of example only, 1, 2, 3, 4, 5, 6, 7, 8, 9, 10, 11, 12, 13, 14, 15, 16, 17, 18, 19, 20, 25, 30, 35, 40, 45, 50, 55, 60, 70, 75, 80, 85, 90, 95, or greater than or equal to 100 capillaries. The capillaries may be attached to one another via a mechanical connecting web 210. In addition, the process of sequentially disposing the first capillary 218A, the second capillary 218B, the third capillary 218C, and the fourth capillary 218D within a receptacle 258 containing a solution 262 comprising and/or consisting of a sample flag compound(s), at least one protein (such as, by way of example only, bovine serum albumin (BSA)), at least one sugar, and at least one alcohol can be accomplished either by a manual or automated process(es) via use of the mechanical web 210. While shown in FIGS. 5A-5H as being identical in configuration, the first capillary 218A, second capillary 218B, the third capillary 218C, and the fourth capillary 218D need not be the same configuration and can be of any size and/or shape that accomplishes the presently disclosed and/or claimed inventive concept(s).

Figure 5A:
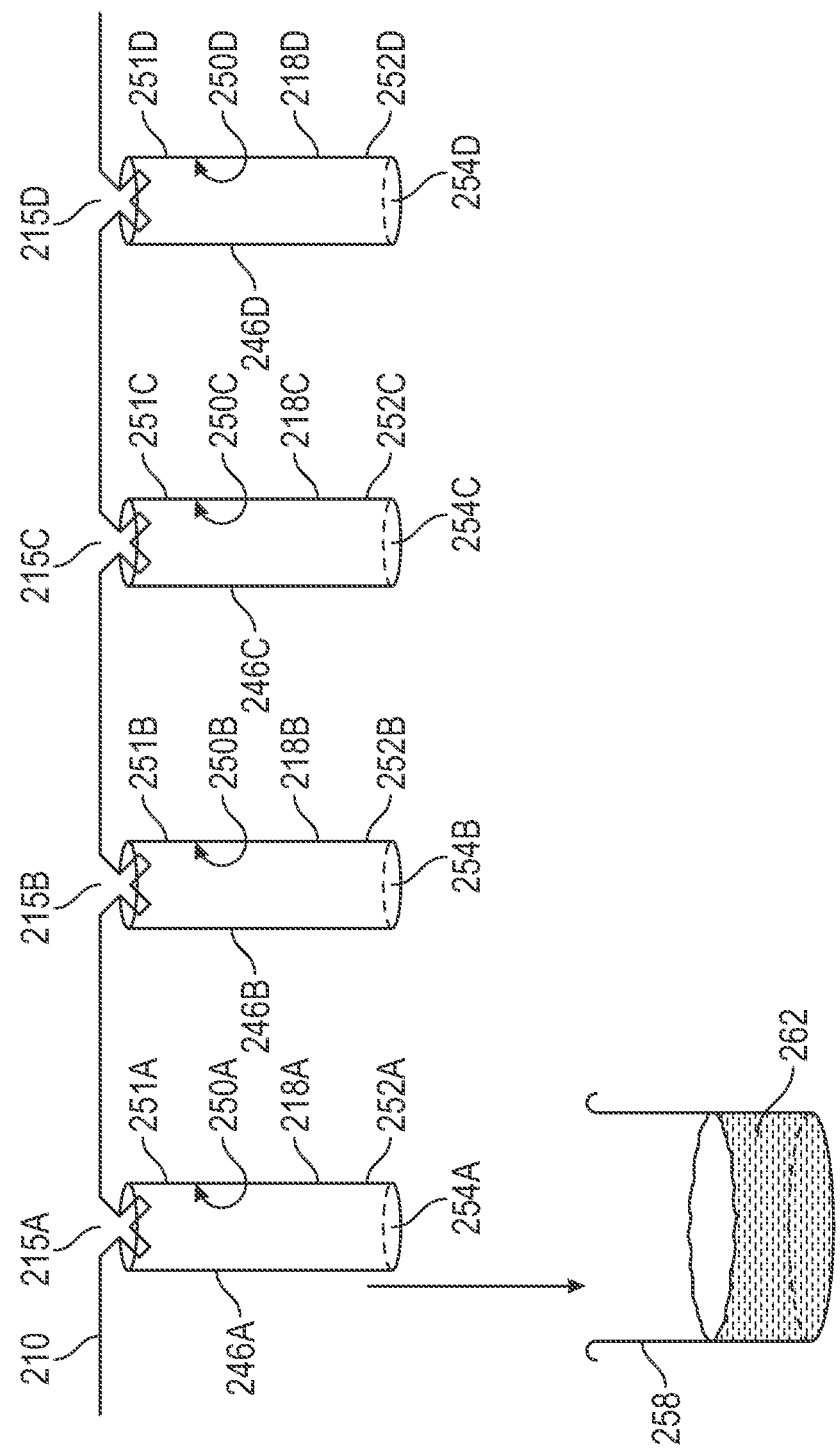
Figure 5B:
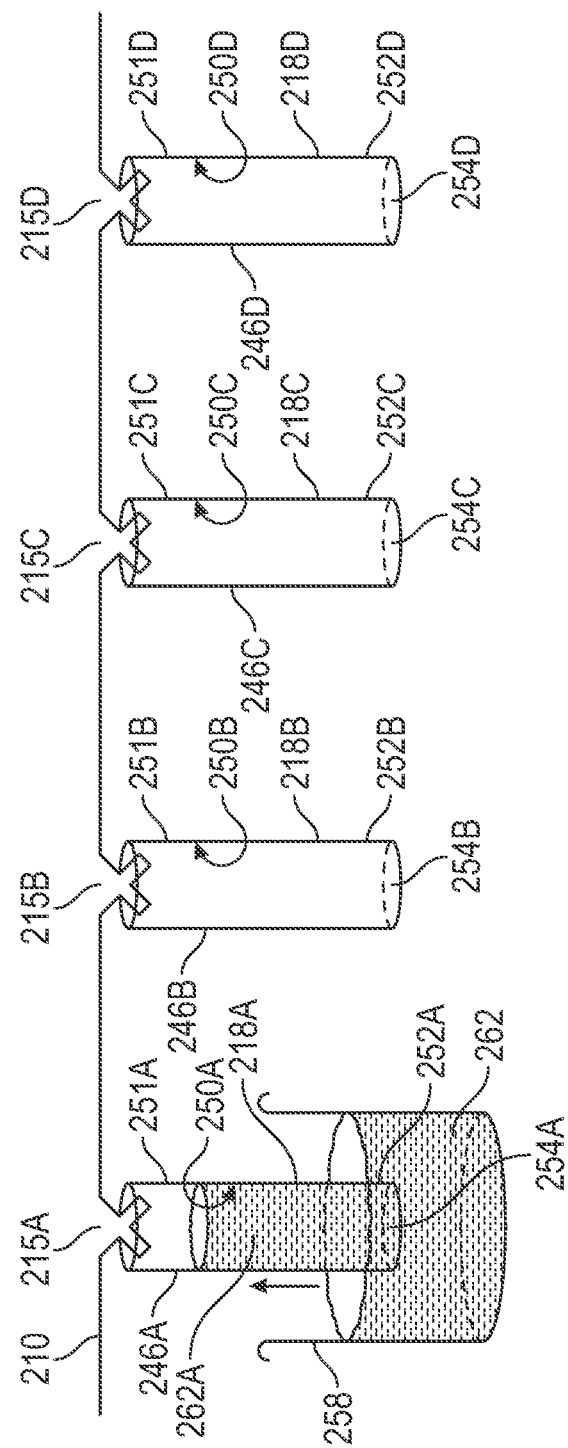

As shown in FIGS. 5A-5B, the first capillary 218A is connected to the mechanical web 210 via, for instance, a first capillary holder 215A. The first capillary 218A comprises at least one outer surface 246A, at least one inner surface 250A, a first end 251A, a second end 252A, and an opening 254A located at the second end 252A for receiving the solution 262 via, by way of example only, capillary action. As shown in FIGS. 5A-5B, the first capillary 218A is lowered from the mechanical web 215 into the receptacle 258 (or, in the alternative, the receptacle 258 is raised to submerge the first capillary 218A) such that the opening 254A is submerged within the solution 262. As a result of this submersion, the solution 262 wicks through the opening 254A (for instance, via capillary action) such that the solution 262 is in fluid contact with at least a portion of the at least one inner surface 250A and remains (as a result of capillary force) within the first capillary 218A for further processing in accordance with the presently disclosed and/or claimed inventive concept(s). After the solution 262 is wicked through the opening 254A of the first capillary 218A, the second capillary 218B is transitioned so that it is capable of being disposed within the receptacle 258.

Figure 5D:
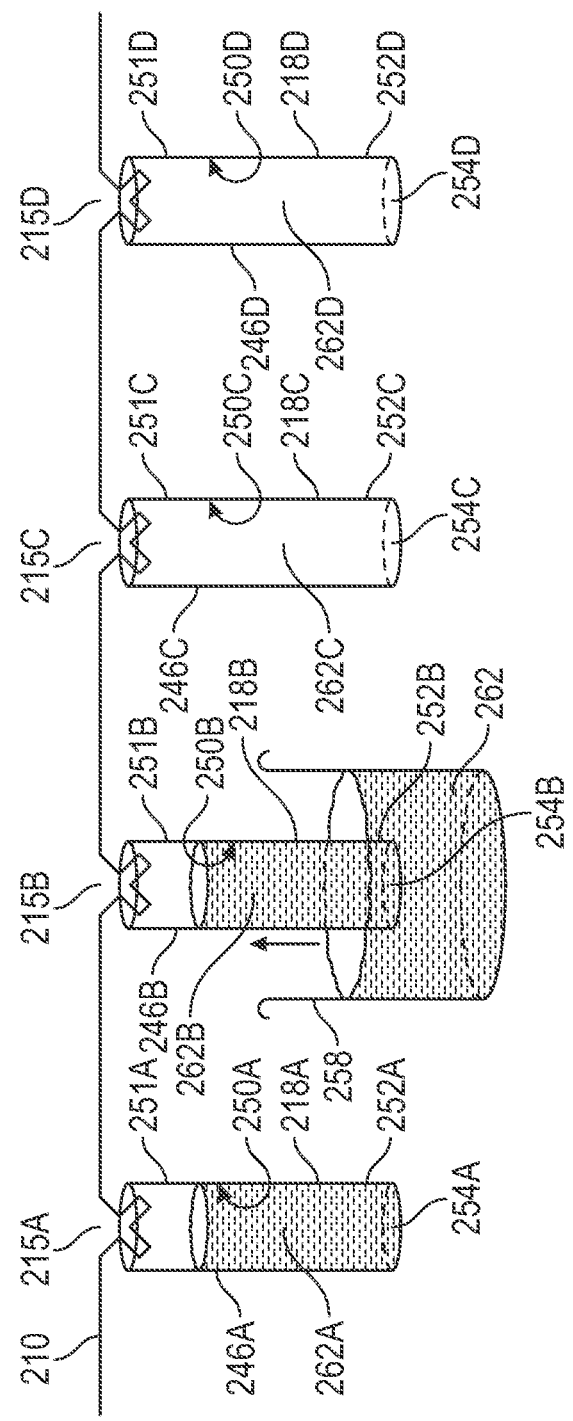

Referring now to FIGS. 5C-5D, the second capillary 218B is connected to the mechanical web 210 via, for instance, a second capillary holder 215B. The second capillary 218B comprises at least outer surface 246B, at least one inner surface 250B, a first end 251B, a second end 252B, and an opening 254B located at the second end 252B for receiving the colloidal solution 262 via, by way of example only, capillary action. As shown in FIGS. 5C-5D, the second capillary 218B is lowered from the mechanical web 215 into the receptacle 258 (or, in the alternative, the receptacle 258 is raised to submerge the second capillary 218B) such that the opening 254B is submerged within the solution 262. As a result of this submersion, the solution 262 wicks through the opening 254B (for instance, via capillary action) such that the solution 262 is in fluid contact with at least a portion of the at least one inner surface 250B and remains (as a result of capillary force) within the second capillary 218B for further processing in accordance with the presently disclosed and/or claimed inventive concept(s). After the solution 262 is wicked through the opening 254B of the second capillary 218B, the third capillary 218C is transitioned so that it is capable of being disposed within the receptacle 258.

Figure 5E:
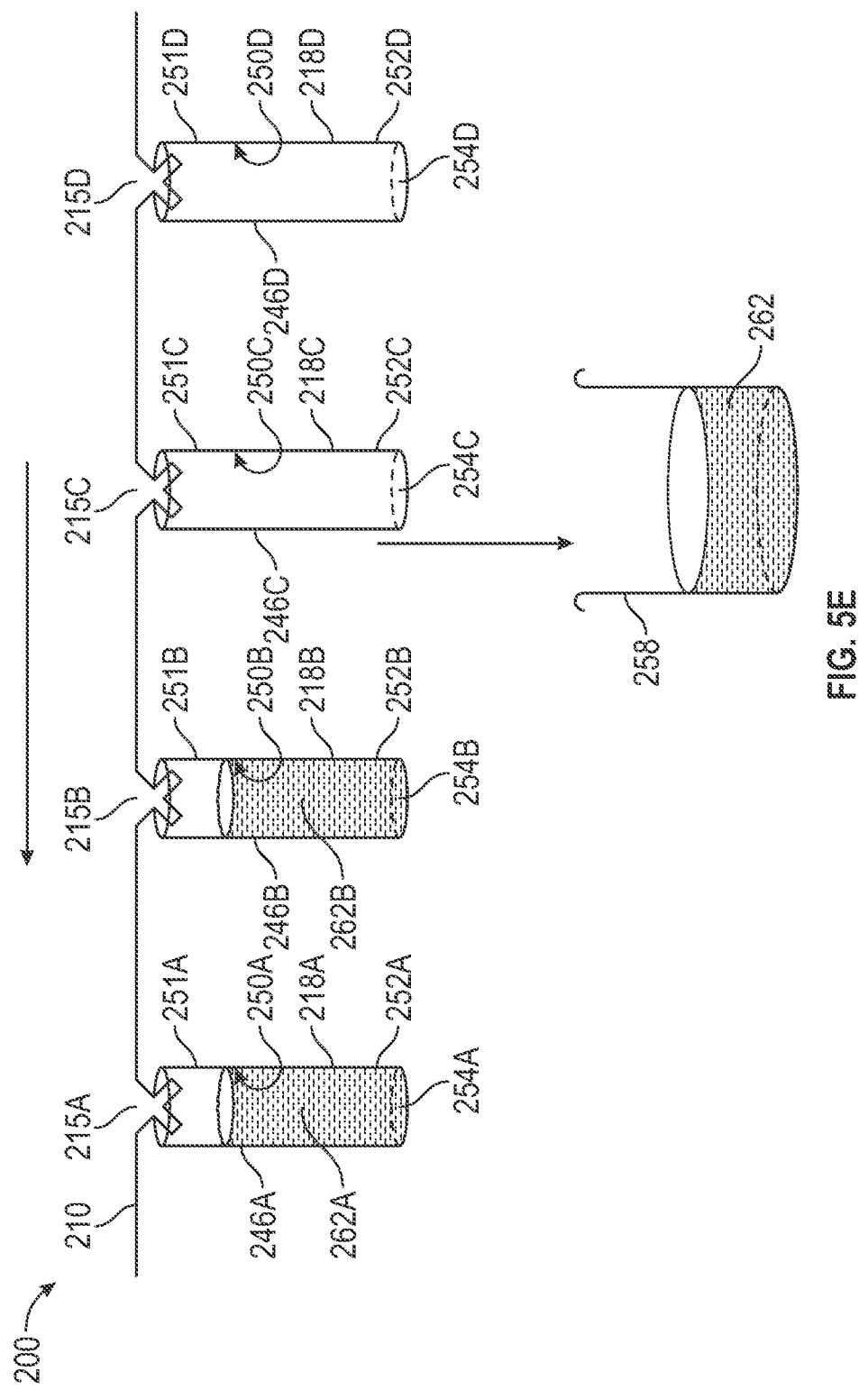
Figure 5F:
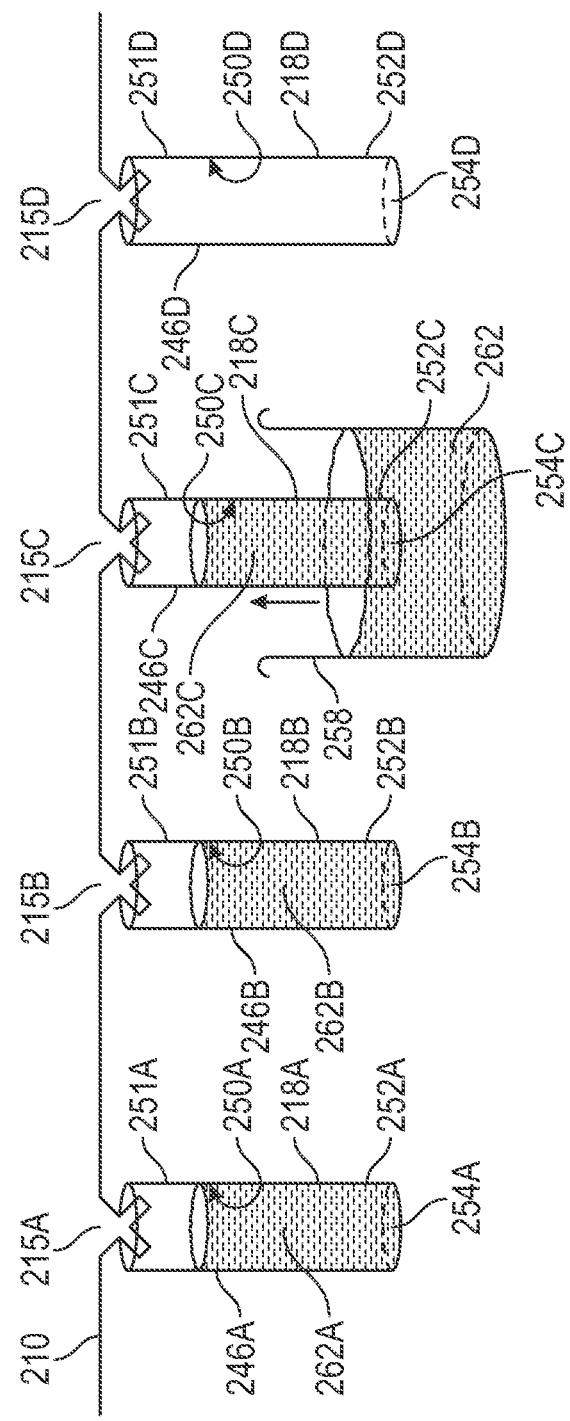

Referring now to FIGS. 5E-5F, the third capillary 218C is connected to the mechanical web 210 via, for instance, a third capillary holder 215C. The third capillary 218C comprises at least outer surface 246C, at least one inner surface 250C, a first end 251C, a second end 252C, and an opening 254C located at the second end 252C for receiving the colloidal solution 262 via, by way of example only, capillary action. As shown in FIGS. 5E-5F, the third capillary 218C is lowered from the mechanical web 215 into the receptacle 258 (or, in the alternative, the receptacle 258 is raised to submerge the third capillary 218C) such that the opening 254C is submerged within the solution 262. As a result of this submersion, the solution 262 wicks through the opening 254C (for instance, via capillary action) such that the solution 262 is in fluid contact with at least a portion of the at least one inner surface 250C and remains (as a result of capillary force) within the third capillary 218C for further processing in accordance with the presently disclosed and/or claimed inventive concept(s). After the solution 262 is wicked through the opening 254C of the third capillary 218B, the fourth capillary 218D is transitioned so that it is capable of being disposed within the receptacle 258.

Figure 5G:
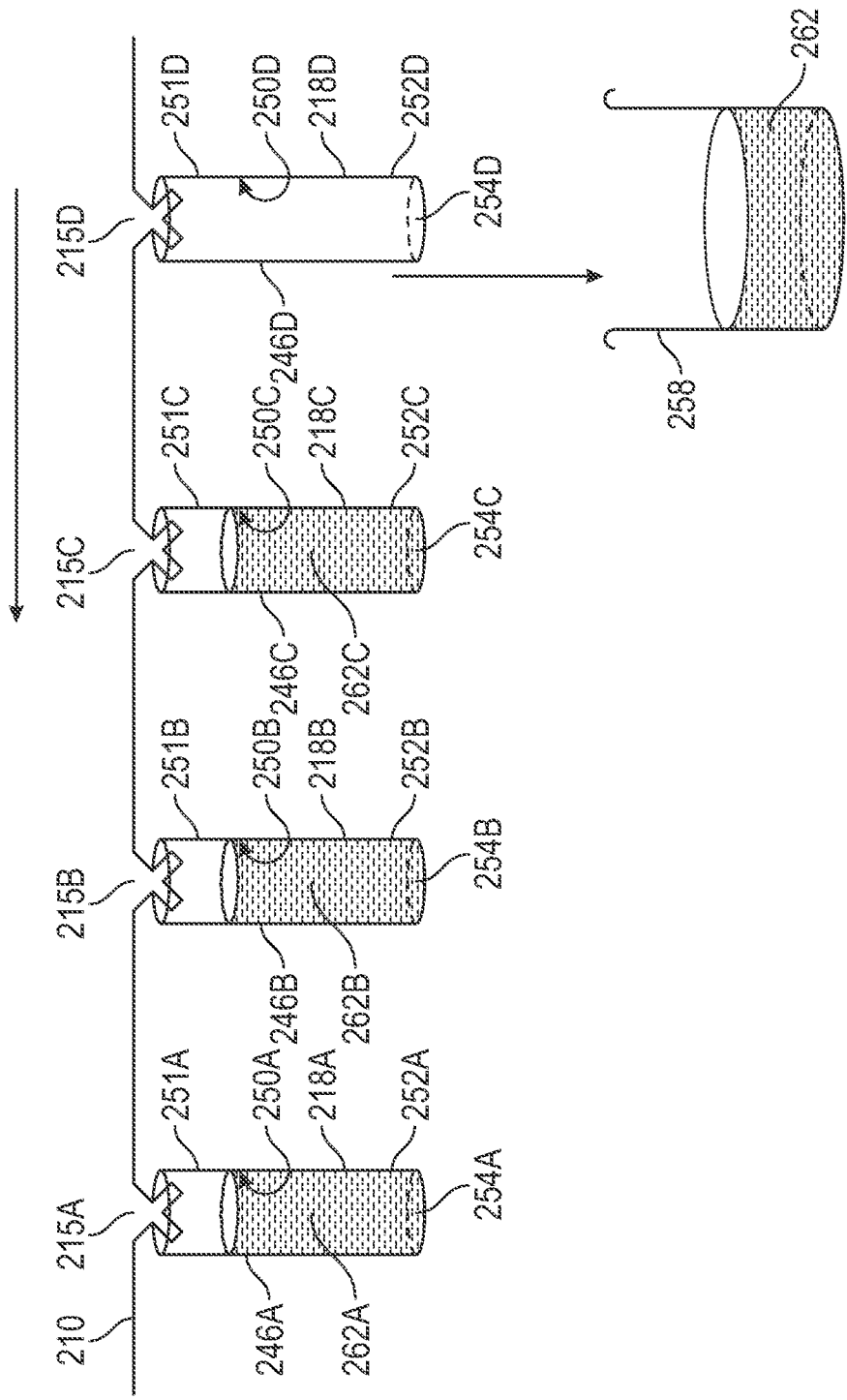
Figure 5H:
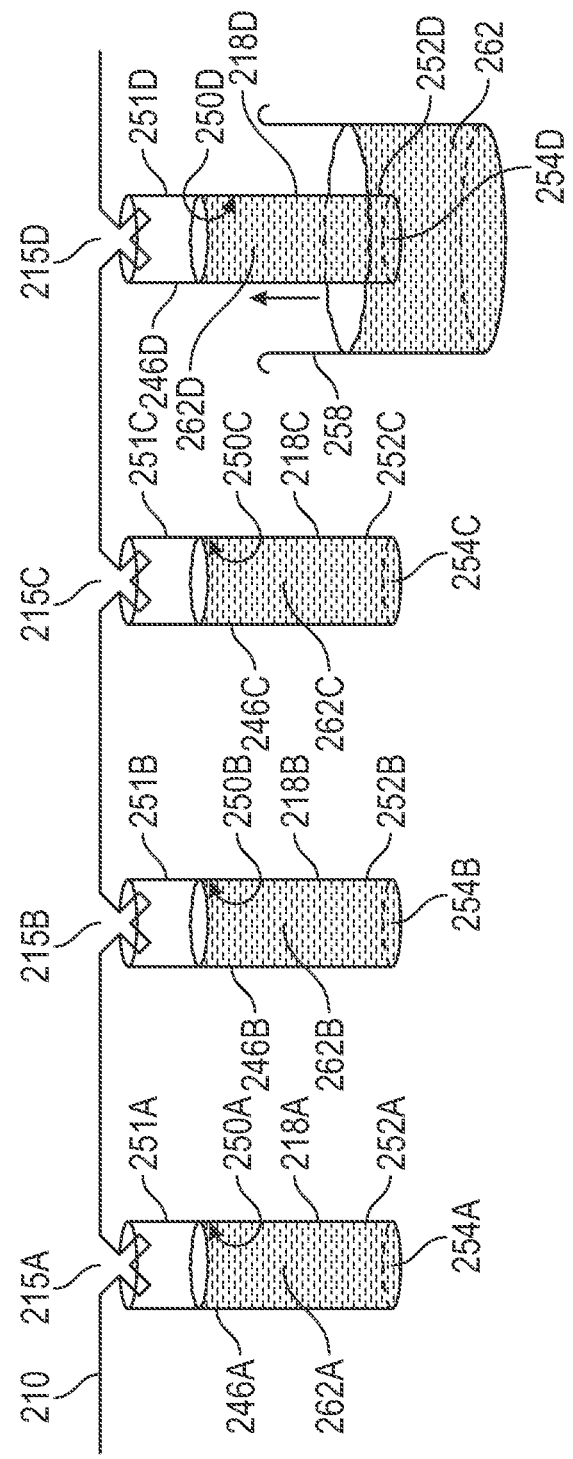

Referring now to FIGS. 5G-5H, the fourth capillary 218D is connected to the mechanical web 210 via, for instance, a fourth capillary holder 215D. The fourth capillary 218D comprises at least outer surface 246D, at least one inner surface 250D, a first end 251D, a second end 252D, and an opening 254D located at the second end 252D for receiving the colloidal solution 262 via, by way of example only, capillary action. As shown in FIGS. 5G-5H, the fourth capillary 218D is lowered from the mechanical web 215 into the receptacle 258 (or, in the alternative, the receptacle 258 is raised to submerge the fourth capillary 218D) such that the opening 254D is submerged within the solution 262. As a result of this submersion, the solution 262 wicks through the opening 254D (for instance, via capillary action) such that the colloidal solution 262 is in fluid contact with at least a portion of the at least one inner surface 250D and remains (as a result of capillary force) within the fourth capillary 218D for further processing in accordance with the presently disclosed and/or claimed inventive concept(s).

The above process is repeated for each capillary attached to the mechanical web 210 such that each capillary contains the solution 262.

Once the solution 262 is contained within the first capillary 218A, the second capillary 218B, the third capillary 218C, and the fourth capillary 218D (and any other capillaries that may be attached to the mechanical web 210), the first capillary 218A, the second capillary 218B, the third capillary 218C, and the fourth capillary 218D (and any other capillaries that may be attached to the mechanical web 201) are heated to evaporate off and remove the alcohol solvent contained within the solution 262. Alternatively, the capillaries may be naturally dried at room temperature to accomplish the evaporation of the alcohol solvent. When the capillaries are heated, the heating can be accomplished via either: (1) by transitioning the mechanical web 210 through a heater such that all of the capillaries are simultaneously heated; and/or (2) by removing the capillaries from the mechanical web and placing them either individually or collectively into a heater. However, at all times, the agitation of the capillaries must be mitigated to ensure that solution 262 remains contained within the capillaries. At this stage, the heating is conducted at a temperature that is high enough to evaporate the alcohol solvent (for instance, an alcohol solvent comprising and/or consisting of methanol, ethanol, isopropyl alcohol, and/or combinations thereof), but low enough so as not to melt the sample flag compound(s) (for instance, ferricyanide-containing compounds, such as potassium ferricyanide granules, which are deposited on the at least one inner surfaces 250A, 250B, 250C, and 250D of each of the capillaries 218A, 218B, 218C, and 218D, respectively, as the alcohol solvent evaporates). In one non-limiting embodiment, the at least one alcohol (solvent) is methanol, ethanol, isopropyl alcohol, and combinations thereof and the solution 262 contained within the capillaries 218A, 218B, 218C, and 218D is heated to and maintained at a temperature from about 20° C. to about 100°, or from about 25° C. to about 95° C., or from about 30° C. to about 90° C., or from about 35° C. to about 85° C., or from about 40° C. to about 80° C., or from about 45° C. to about 75° C., or from about 50° C. to about 70° C., or from about 55° C. to about 65° C., or greater than or equal to about 60° C. In one non-limiting embodiment, the capillaries 218A-218D are heated to a temperature of about 25° C. to about 37° C. to evaporate off and remove the at alcohol solvent from the solution 262 contained within the capillaries 218A-218D. The capillaries 218A-218D can be heated via any method commonly known in the art provided that the colloidal solution 262 remains in contact with each of the at least one inner surfaces 250A-250D of the capillaries 218A-218D prior to and during the evaporation of the at least one alcohol (solvent), including, without limitation, via commercial-grade dryers and/or vacuum dryers commonly known in the art.

Following the evaporation of the at least one alcohol (solvent) from the at least one inner surfaces 250A-250D of the capillaries 218A-218D, a sample flag compound(s) (for instance, ferricyanide-containing compounds, such as potassium ferricyanide granules) is deposited on the at least one inner surfaces 250A, 250B, 250C, and 250D of each of the capillaries 218A, 218B, 218C, and 218D, respectively At this stage, the capillaries 218A-218D are ready to be attached to their respective liquid test sample dispensing devices for the collection of a patient's liquid test sample for the conductance of at least one diagnostic assay or to be used for additional applications contemplated by the presently disclosed and/or claimed inventive concept(s).

Certain non-limiting embodiments of the presently disclosed and/or claimed inventive concept(s) include, but are not limited to the following:

A capillary internally coated with at least one sample flag compound for use in at least one diagnostic assay, comprising: at least one capillary, the capillary having at least one outer surface, at least one inner surface, a first end, a second end, and opening located at the second of the capillary, wherein at least a portion of the inner surface of the capillary is coated with at least one sample flag compound, the at least one sample flag compound detecting the presence or non-presence of a patient's liquid test sample within the capillary.

The capillary, wherein the at least one sample flag compound is selected from the group consisting of ferricyanide, metabisulfite, taurine, and combinations thereof.

The capillary, wherein the patient's liquid test sample is urine.

The capillary, wherein the at least diagnostic assay comprises a microalbumin creatinine diagnostic assay A method for coating at least one internal surface of a capillary of a liquid test sample dispensing device with at least one sample flag compound, the method comprising the steps of: preparing a solution, the solution comprising at least one sample flag compound, at least one protein, at least one sugar, and at least one alcohol solvent, the solution being contained within a receptacle; placing a liquid test sample dispensing device into the receptacle, the liquid test sample dispensing device comprising: a capillary portion, the capillary portion comprising a capillary having at least one outer surface, at least one inner surface, a first end, a second end, and an opening located at the second end of the capillary, wherein the capillary is in fluid contact with the solution such that a volume of the solution enters into and is retained within the capillary via the opening such that the solution is in fluid contact with the at least one inner surface of the capillary; and removing the liquid test sample dispensing device from the receptacle and heating at least the capillary portion of the liquid test sample dispensing device to a temperature wherein the at least one alcohol solvent evaporates from the solution contained within the capillary, and further wherein granules of the at least one sample flag compound are deposited on the at least one inner surface of the capillary.

The method, wherein the at least one sample flag compound is dissolved upon contact with a patient's liquid test sample to thereby form a sample mixture.

The method, wherein the at least one sample flag compound is selected from the group consisting of ferricyanide, metabisulfite, taurine and combinations thereof.

The method, wherein the at least one protein comprises bovine serum albumin (BSA).

The method, wherein the at least one sugar is selected from the group consisting of monosaccharides, disaccharides, oligosaccharides, polysaccharides, and combinations thereof.

The method, wherein the at least one sugar is selected from the group consisting of fructose, galactose, glucose, lactose, maltose, sucrose, and combinations thereof.

The method, wherein the at least one alcohol solvent is selected from the group consisting of monohydric, polyhydric, unsaturated aliphatic, alicyclic alcohols, and combinations thereof.

The method, wherein the at least one alcohol solvent is selected from the group consisting of methanol, ethanol, propanol, butanol, pentanol, cetyl alcohol, ethylene glycol, propylene glycol, glycerol, erythritol, xylitol, mannitol, volemitol, allyl alcohol, geraniol, propargyl alcohol, inositol, menthol, and combinations thereof.

The method, wherein volume of the solution entering into and retained within the capillary is about 35 microliters.

The method, wherein the temperature to which the liquid test sample dispensing device is heated is in a range of from about 25° C. to about 37° C.

The method, wherein the capillary portion is heated via a heater selected from the group consisting of a commercial-grade dryer, a vacuum dryer, and combinations thereof.

A method for detecting the presence or non-presence of a patient's liquid test sample within a liquid test sample dispensing device prior to the conductance of at least one diagnostic assay, the method comprising the steps of: securing a liquid test sample dispensing device within a reaction vessel, the liquid test sample dispensing device comprising: a capillary portion, the capillary portion comprising a capillary having at least one outer surface, at least one inner surface, a first end, a second end, and an opening located at the second end of the capillary, wherein at least a portion of the inner surface of the capillary is substantially coated with at least one sample flag compound, the at least one sample flag compound dissolving when in contact with a patient's liquid test sample to thereby form a sample mixture comprising the patient's liquid test sample and the at least one dissolved sample flag compound; inserting the reaction vessel into a diagnostic assay analyzer; interrogating at least the capillary portion of the liquid test sample dispensing device with at least one predetermined wavelength of light; and measuring a detectable signal generated from the interrogation of the sample mixture, the sample mixture generating the detectable signal only when a patient's liquid test sample is present within capillary of the liquid test sample dispensing device.

The method, wherein the at least one sample flag compound is selected from the group consisting of ferricyanide, metabisulfite, taurine and combinations thereof.

The method, wherein the at least one protein comprises bovine serum albumin (BSA).

The method, wherein the at least one sugar is selected from the group consisting of monosaccharides, disaccharides, oligosaccharides, polysaccharides, and combinations thereof.

The method, wherein the at least one sugar is selected from the group consisting of fructose, galactose, glucose, lactose, maltose, sucrose, and combinations thereof.

The method, wherein the at least one alcohol solvent is selected from the group consisting of monohydric, polyhydric, unsaturated aliphatic, alicyclic alcohols, and combinations thereof.

The method, wherein the at least one alcohol solvent is selected from the group consisting of methanol, ethanol, propanol, butanol, pentanol, cetyl alcohol, ethylene glycol, propylene glycol, glycerol, erythritol, xylitol, mannitol, volemitol, allyl alcohol, geraniol, propargyl alcohol, inositol, menthol, and combinations thereof.

The method, wherein the temperature to which the liquid test sample dispensing device is heated is in a range of from about 25° C. to about 37° C.

The method, wherein the capillary portion is heated via a heater selected from the group consisting of a commercial-grade dryer, a vacuum dryer, and combinations thereof.

The method, wherein the predetermined wavelength of light is in the range of from about 380 nanometers to about 800 nanometers.

The method, wherein the predetermined wavelength of light is about 425 nanometers.

The method, wherein the detectable signal generated from the interrogation of the sample mixture is a change in absorbance.

The method, wherein the interrogation of at least the capillary portion of the liquid test sample dispensing device with a predetermined wavelength of light occurs via at least one LED light source.

The method, wherein the patient's liquid test sample is urine.

The method, wherein the at least one diagnostic assay comprises a microalbumin creatinine diagnostic assay.

NON-LIMITING EXAMPLES OF THE INVENTIVE CONCEPT(S)

Experimental Preparation and Setup No. 1

In Experimental Preparation and Setup No. 1, the solutions, intermediaries, and final capillary(-ies) were at all times protected from exposure to violet-ultraviolet (UV) light.

Solution 1 Composition: 15 milligram/milliliter potassium ferricyanide, 6% bovine serum albumin (BSA), and 15% sucrose.

Solution 2 Composition: methanol, ethanol, isopropyl alcohol, or other water-soluble compound with low FeCN solubility.

Solution 1 and solution 2 are mixed with one another to thereby form a combined solution in which the ratio of solution 1 to solution 2 is about 2.58:32.42.

Figure 6:
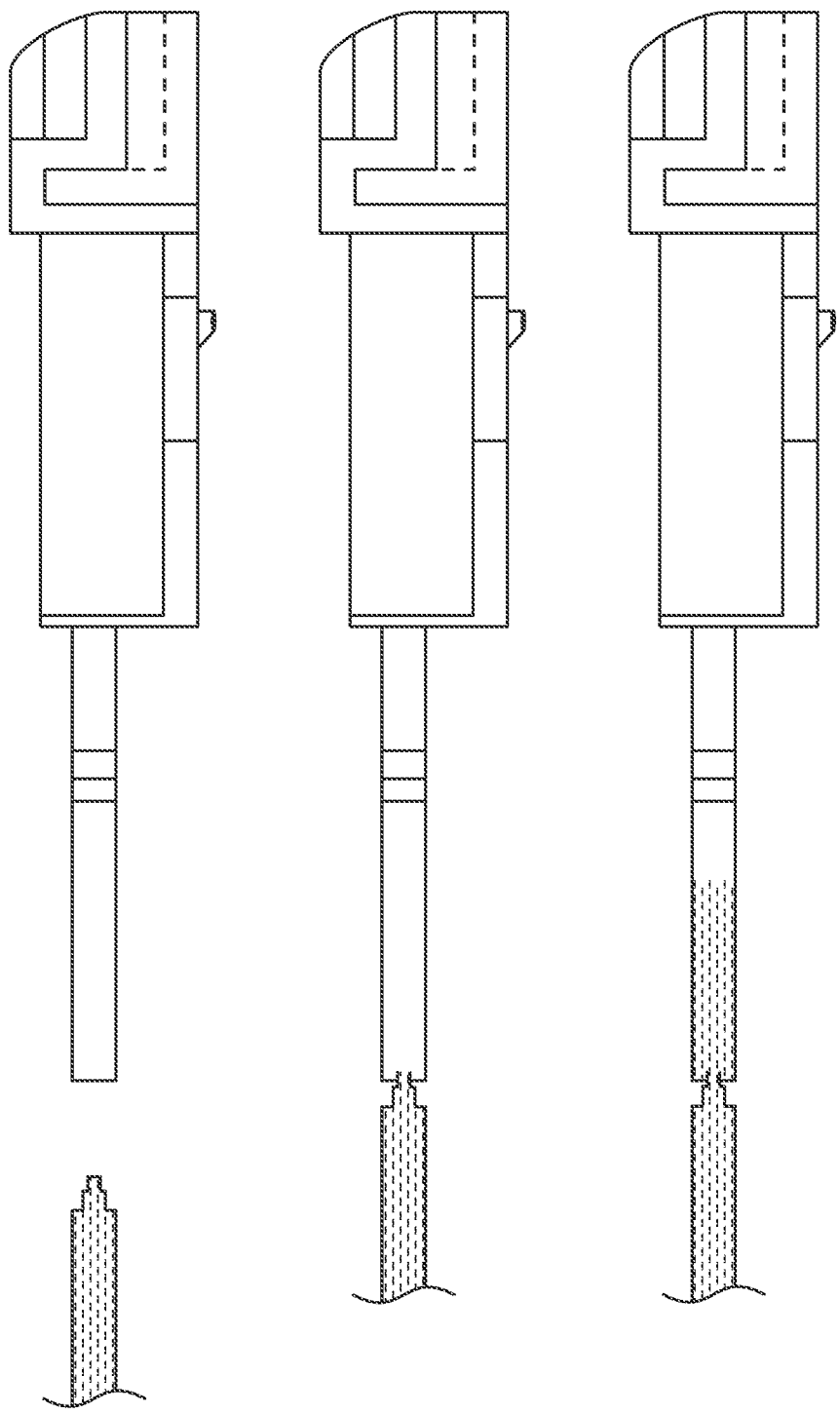
FIG. 6 shows a non-limiting embodiment of an experimental setup utilized in accordance with the presently disclosed and/or claimed inventive concept(s) in which the combined solution is injected into a capillary.

About 35 microliters of the combined solution (as shown in FIG. 6) was injected via pipette into the opening of the capillary to thereby bring the combined solution into fluid contact with at least one inner surface of the capillary. Following injection of the combined sample into the capillary, the capillary was subsequently dried to evaporate the alcohol solvent (and at least portions of the BSA and sucrose) and deposit potassium ferricyanide (sample flag) granules on the at least one inner surface of the capillary.

Once the ferricyanide sample flag compound has been deposited on the at least one inner surface of the capillary, a patient's urine sample is drawn into the capillary whereby the urine sample mixes with and dissolves the ferricyanide sample flag compound to thereby form a sample mixture. The capillary containing the sample mixture was then interrogated with three different wavelengths of light (425 nanometers, 536 nanometers, and 725 nanometers) and various measurements, including, without limitation, absorbance (and changes thereto) associated with the sample mixture were obtained.

Experimental Results.

Figure 7:
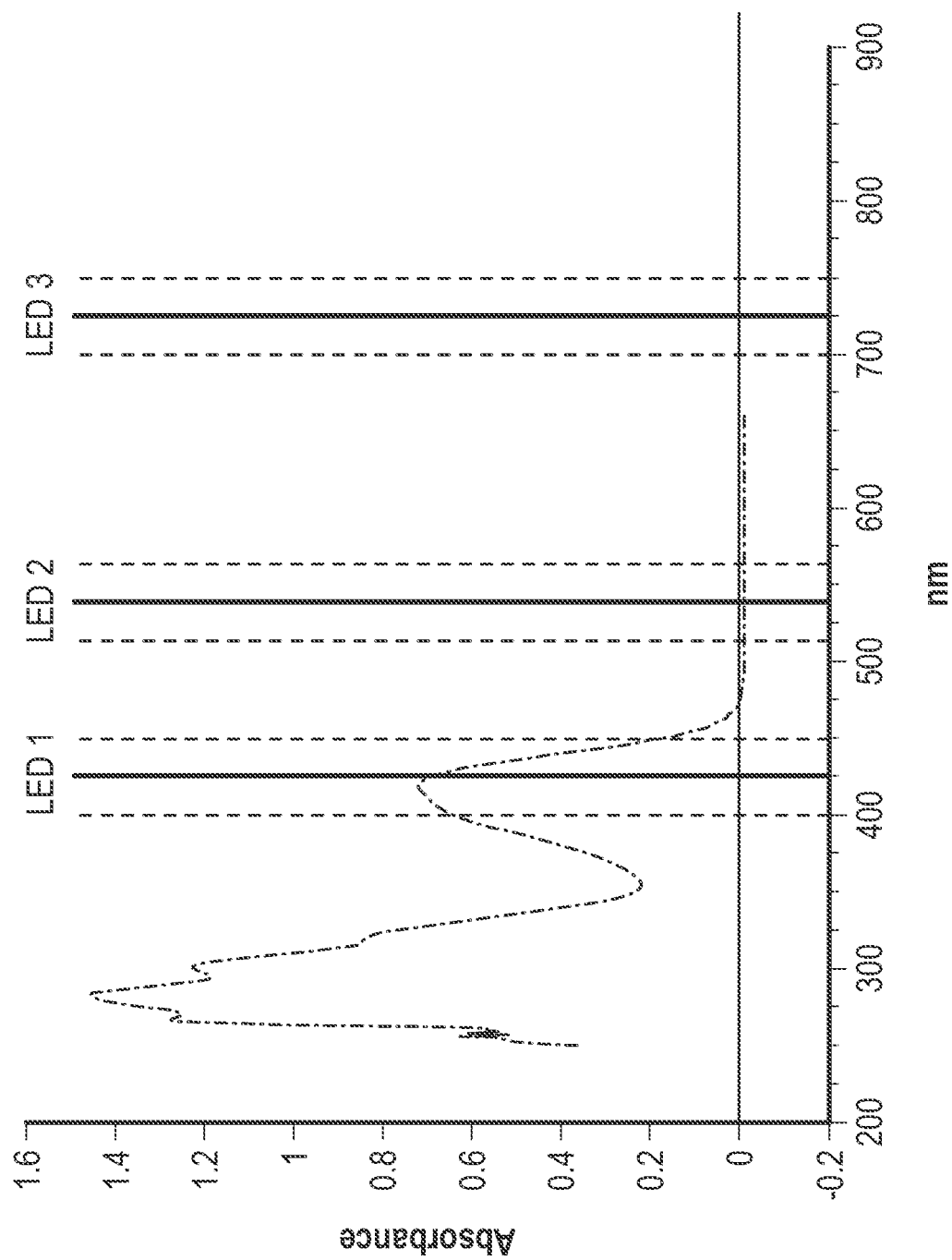
FIG. 7 depicts a graphical representation showing the centroid and approximate full width half max (FWHM) of three LED lights present in diagnostic assay system/instrument overlaid on the spectrum of the ferricyanide sample flag compound in accordance with the presently disclosed and/or claimed inventive concept(s).
Figure 8:
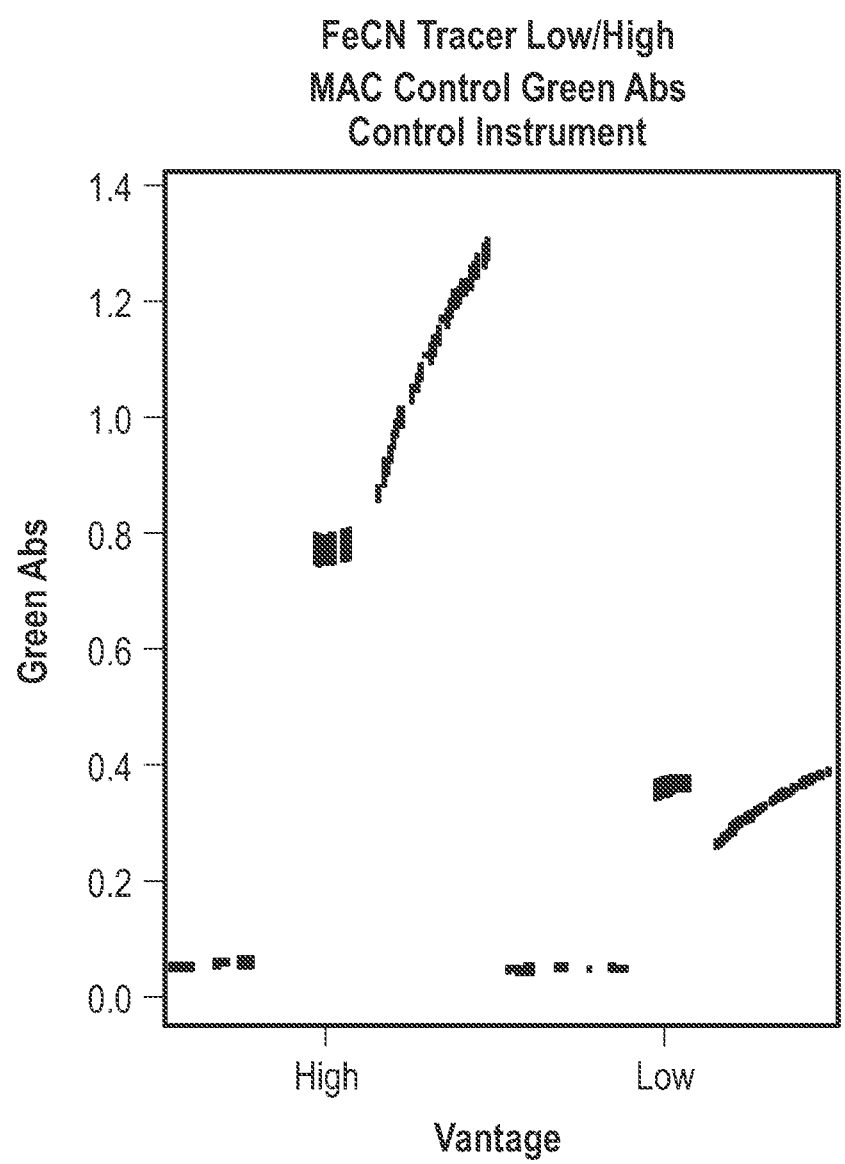
FIG. 8 depicts a graphical representation showing that the addition of a ferricyanide sample flag does not negatively impact the range of the diagnostic assay's high and low control solutions.
Figure 9:
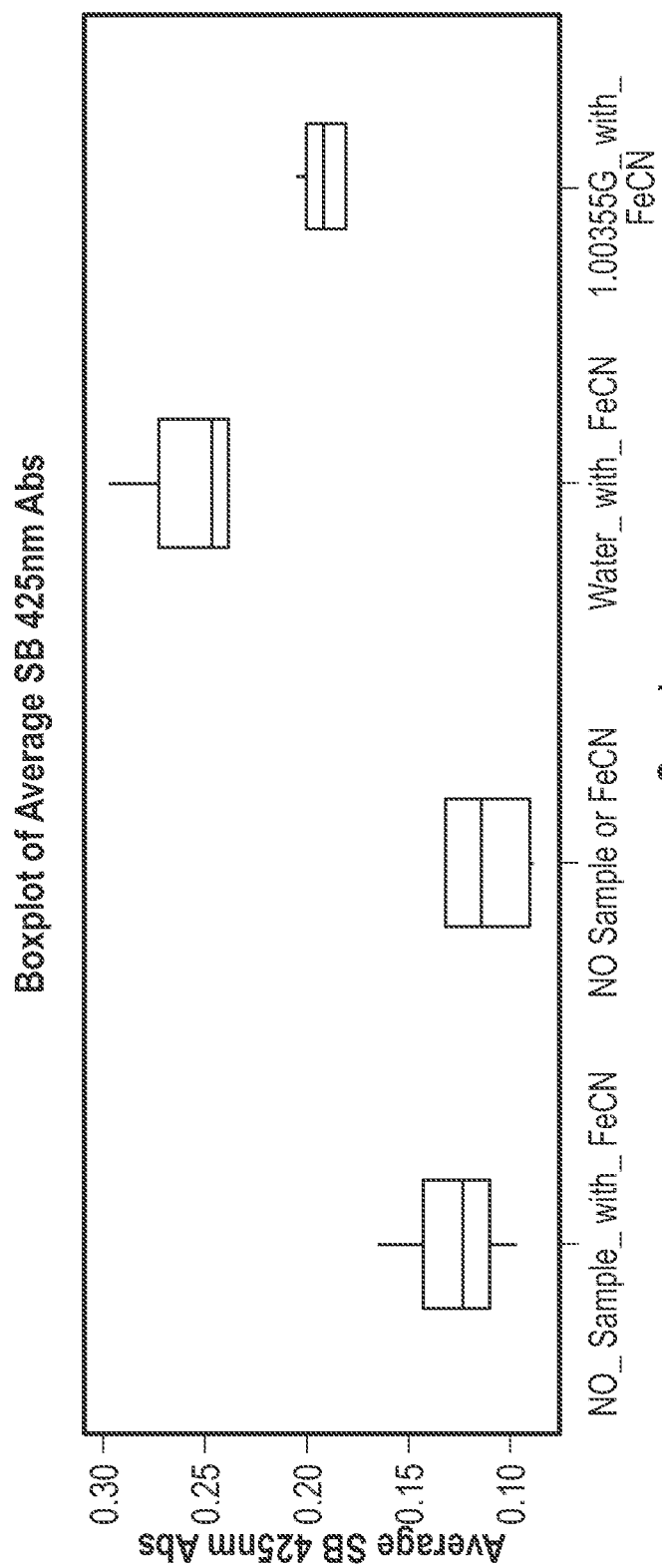
FIG. 9 depicts a boxplot graphical representation showing the average absorbance readings of various mixtures of a ferricyanide sample flag compound (with and without mixture of a patient's liquid test sample) at a wavelength of about 425 nanometers in accordance with the presently disclosed and/or claimed inventive concept(s).
Figure 10:
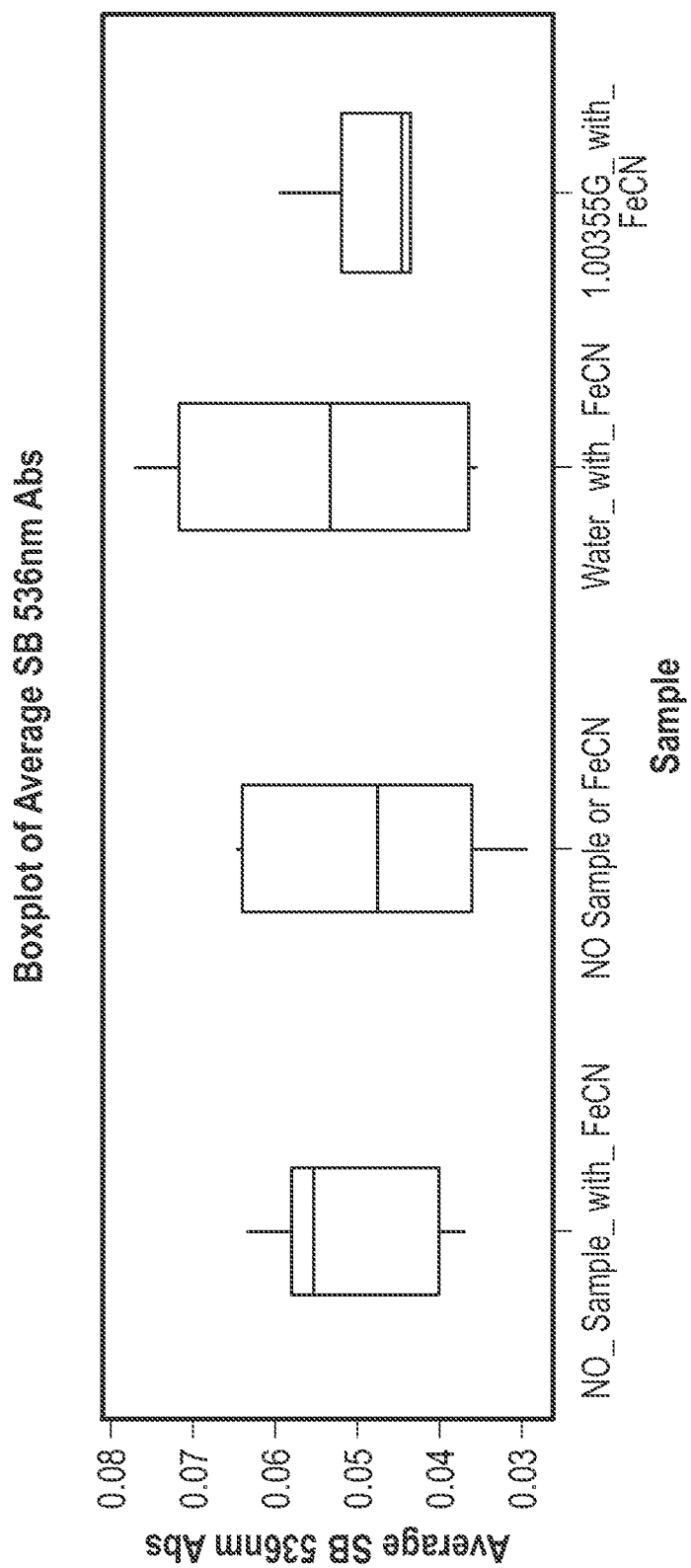
FIG. 10 depicts a boxplot graphical representation showing the average absorbance readings of various mixtures of a ferricyanide sample flag compound (with and without mixture of a patient's liquid test sample) at a wavelength of about 536 nanometers in accordance with the presently disclosed and/or claimed inventive concept(s).

Referring now to FIG. 7, shown therein is a graphical representation showing the centroid and approximate full width half max (FWHM) of three LED lights present in diagnostic assay system/instrument overlaid on the spectrum of the ferricyanide sample flag. As can be clearly seen in FIG. 7, the sample mixture exhibits an absorbance shift of about 0.7 when interrogated with a LED light having a wavelength of about 425 nanometers. Conversely, the sample mixture does not show any absorbance shift when interrogated with LED lights having wavelengths of about 536 nanometers and 725 nanometers, respectively. Accordingly, the ferricyanide sample flag compound serves as a robust sample flag to detect the presence of a patient's liquid test sample (such as, by way of example only, a urine sample) at a wavelength in the 425-nanometer region without interfering with longer wavelengths (which are or can be reserved for diagnostic assay reaction(s) monitoring). When there is no liquid test sample in the capillary, the 425-nanometer absorbance of the sample flag compound does not appear thereby alerting the diagnostic assay system/instrument that an error has occurred (such as, by way of example only, the operator neglected to collect the patient's liquid test sample within the capillary). These results are further shown and confirmed in FIGS. 8-11.

Thus, in accordance with the presently disclosed and claimed inventive concept(s), there have been provided devices, kits, and methods that utilize at least one sample flag compound for the detection (and/or verification of the presence) of a patient's liquid test sample within a liquid test sample dispensing device for use in the conductance of at least one diagnostic assay. As described herein, the presently disclosed and claimed inventive concept(s) relate to embodiments of an improved liquid test sample injection device comprising and/or consisting of at least one sample flag compound present within and coated on at least one inner surface of the capillary, the at least one sample flag compound emitting a detectable signal when interrogated by a predetermined wavelength of light in the presence of a patient's liquid test sample. Such presently disclosed and/or claimed inventive concept(s) fully satisfy the objectives and advantages set forth hereinabove. Although the presently disclosed and claimed inventive concept(s) has been described in conjunction with the specific drawings, experimentation, results and language set forth hereinabove, it is evident that many alternatives, modifications, and variations will be apparent to those skilled in the art. Accordingly, it is intended to embrace all such alternatives, modifications and variations that fall within the spirit and broad scope of the presently disclosed and claimed inventive concept(s).

What is claimed is:

1. A method for preparing a diagnostic assay device for performing at least one diagnostic assay on a liquid test sample, the diagnostic assay device comprising a reaction vessel having a liquid test sample dispensing device inserted into a portion thereof, wherein the liquid test sample dispensing device is configured for collecting the liquid test sample and dispensing the liquid test sample into the reaction vessel for performing at least one diagnostic assay in the reaction vessel, the method comprising the steps of:
   (a) preparing a solution, the solution comprising at least one sample flag compound, at least one protein, at least one sugar, and at least one alcohol solvent, the solution being contained within a receptacle;

(b) placing the liquid test sample dispensing device into the receptacle, the liquid test sample dispensing device comprising:

a capillary portion, the capillary portion comprising a capillary having at least one outer surface, at least one inner surface, a first end, a second end, and an opening located at the second end of the capillary, wherein the capillary is in fluid contact with the solution such that a volume of the solution enters into and is retained within the capillary via the opening such that the solution is in fluid contact with the at least one inner surface of the capillary; and (c) removing the liquid test sample dispensing device from the receptacle and heating at least the capillary portion of the liquid test sample dispensing device to a temperature wherein the at least one alcohol solvent evaporates from the solution contained within the capillary, and further wherein granules of the at least one sample flag compound are deposited on the at least one inner surface of the capillary, thereby coating the at least one internal surface of the capillary with the at least one sample flag compound; and (d) inserting and securing the liquid test sample dispensing device in the reaction vessel to form the diagnostic assay device, wherein the reaction vessel comprises at least one sample read window for interrogation of the at least one sample flag compound in the capillary at a first wavelength of light, and wherein the reaction vessel further comprises a reaction chamber containing at least one diagnostic assay reagent that is interrogated at a second wavelength of light that is different from the first wavelength.

2. The method of claim 1, wherein the at least one sample flag compound is dissolvable in the presence of a patient's liquid test sample selected from the group consisting of whole blood, plasma, serum, and urine.

3. The method of claim 1, wherein the at least one sample flag compound is selected from the group consisting of ferricyanide, metabisulfite, taurine and combinations thereof.

4. The method of claim 1, wherein the at least one protein comprises bovine serum albumin (BSA).

5. The method of claim 1, wherein the at least one sugar is selected from the group consisting of monosaccharides, disaccharides, oligosaccharides, polysaccharides, and combinations thereof.

6. The method of claim 5, wherein the at least one sugar is selected from the group consisting of fructose, galactose, glucose, lactose, maltose, sucrose, and combinations thereof.

7. The method of claim 1, wherein the at least one alcohol solvent is selected from the group consisting of monohydric, polyhydric, unsaturated aliphatic, alicyclic alcohols, and combinations thereof.

8. The method of claim 7, wherein the at least one alcohol solvent is selected from the group consisting of methanol, ethanol, propanol, butanol, pentanol, cetyl alcohol, ethylene glycol, propylene glycol, glycerol, erythritol, xylitol, mannitol, volemitol, allyl alcohol, geraniol, propargyl alcohol, inositol, menthol, and combinations thereof.

9. The method of claim 1, wherein volume of the solution entering into and retained within the capillary is about 35 microliters.

10. The method of claim 1, wherein the temperature to which the liquid test sample dispensing device is heated is in a range of from about 25° C. to about 37° C.

11. The method of claim 10, wherein the capillary portion is heated via a heater selected from the group consisting of a commercial-grade dryer, a vacuum dryer, and combinations thereof.

12. The method of claim 1, wherein the at least one diagnostic assay comprises a microalbumin creatinine diagnostic assay.

* * * * *